United States Patent [19]

Petersen

[11] Patent Number: 4,683,000
[45] Date of Patent: Jul. 28, 1987

[54] HERBICIDAL SULFONAMIDES

[75] Inventor: W. Christian Petersen, Hockessin, Del.

[73] Assignee: E. I. Du Pont de Nemours and Comany, Wilmington, Del.

[21] Appl. No.: 564,379

[22] Filed: Dec. 22, 1983

[51] Int. Cl.[4] .................... C07D 403/12; A01K 47/36
[52] U.S. Cl. ........................................ 71/92; 544/321; 544/323; 544/324; 544/331; 544/332; 71/93
[58] Field of Search ............... 544/331, 332, 321, 324, 544/323; 71/92

[56] References Cited

U.S. PATENT DOCUMENTS

| 4,484,939 | 11/1984 | Tseng | 71/92 |
| 4,492,596 | 1/1985 | Pasteris | 71/40 |
| 4,589,911 | 5/1986 | Ehrenfreund | 71/91 |

FOREIGN PATENT DOCUMENTS

| 79683 | 5/1983 | European Pat. Off. | 548/331 |
| 99339 | 1/1984 | European Pat. Off. | 548/331 |

*Primary Examiner*—Robert Gerstl

[57] ABSTRACT

Novel N-(heterocyclicaminocarbonyl)arylsulfonamides such as 2,3-dihydro-N-[(4-methoxy-6-methyl-1,3,5-triazin-2-yl)aminocarbonyl]-1H-indole-7-sulfonamide are useful as pre-emergence and post-emergence herbicides and for the regulation of plant growth.

16 Claims, No Drawings

HERBICIDAL SULFONAMIDES

BACKGROUND OF THE INVENTION

The invention relates to certain novel sulfonamide compounds, to compositions containing such compounds. and to methods-of-use of such compounds to control the growth of undesired vegetation.

U.S Pat. Nos. 4,127,405 issued Nov. 28, 1978, and 4,169,719, issued Oct. 2, 1979, both patents to Levitt, disclose certain substituted heterocyclic aryl sulfonylurea compounds and provides basic information pertaining to sulfonylurea compounds.

EPO Publication No. 70,698, published Jan. 26, 1983 teaches herbicidal indole sulfonylureas represented by the general formulas shown below.

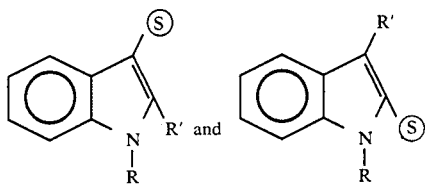

wherein
S is $SO_2NHCONH$-Het;
R may be H or alkyl:
R' may be H, alkyl or a carboxylic acid ester.

U.S. Pat. No. 4,369,320 teaches herbicidal quinoline sulfonylureas such as the following structure:

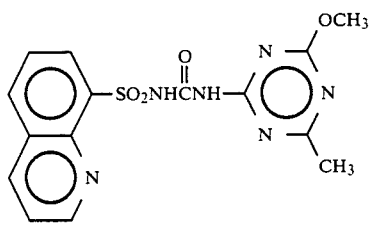

EPO Publication No. 79,683, published May 25, 1983 teaches dihydrobenzofuran and dihydrobenzothiophene sulfonylureas such as:

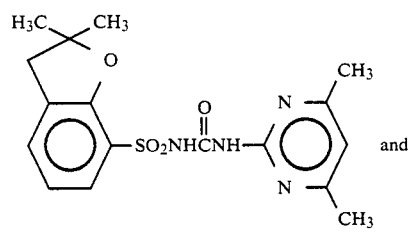

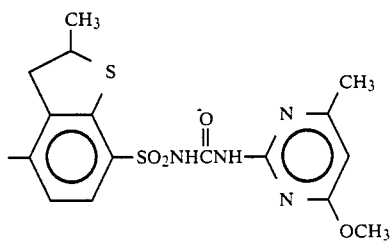

U.S. Pat. No. 4,369,058 teaches herbicidal benzenesulfonylureas of the general formula:

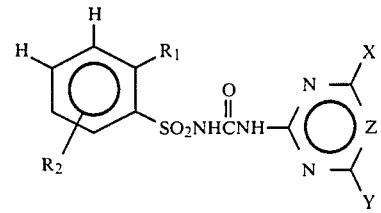

wherein
$R_1$ may be H;
$R_2$ may be $NR_6R_7$;
$R_6$ is H or alkyl of 1–3 carbon atoms;
$R_7$ is H or alkyl of 1–3 carbon atoms or $R_6$ and $R_7$ taken together are $-(CH_2)_{4-5}-$ or $-CH_2Ch_2OCH_2CH_2-$.

The compounds of the present application are not disclosed in the above publications or issued patents.

SUMMARY OF THE INVENTION

This invention relates to novel compounds of Formula I, suitable agricultural compositions containing them and their method-of-use as general pre-emergence or post-emergence herbicides or plant growth regulants.

$$LSO_2NHCNA \atop R \qquad \qquad I$$

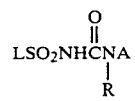

wherein
L is

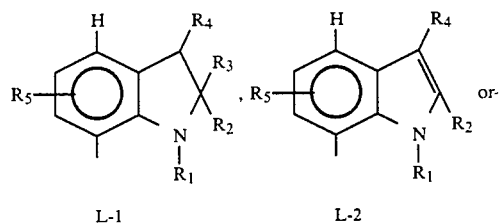

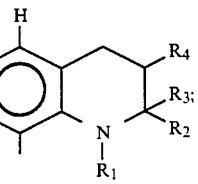

R is H or $CH_3$;
$R_1$ is H, $C_1$–$C_3$ alkyl or $C_3$ alkenyl;
$R_2$ is H, $C_1$–$C_3$ alkyl, $CO_2R_7$ or $CON(CH_3)_2$;
$R_3$ is H or $CH_3$;
$R_4$ is H or $CH_3$;
$R_5$ is H, $CH_3$, $CH_2CH_3$, F, Cl, Br, $OCH_3$, $OCF_2H$, $SCH_3$, $SCF_2H$ or $CF_3$;
$R_6$ is H, $CH_3$, $CH_2CH_3$, F, Cl, Br, $OCH_3$, $OCF_2H$, $SCH_3$, $SCF_2H$ or $CF_3$;
$R_7$ is $CH_3$ or $CH_2CH_3$;
A is

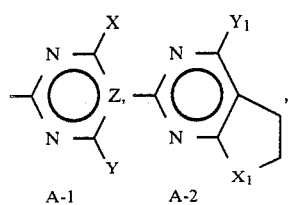

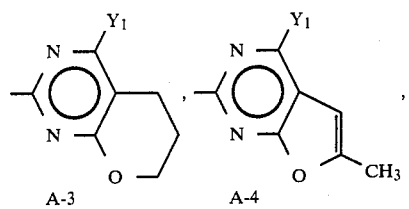

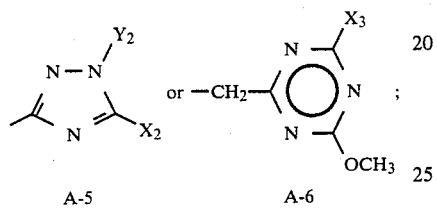

X is Cl, Br, C$_1$-C$_2$ alkyl, C$_1$-C$_2$ alkoxy, OCF$_2$H or CF$_3$;
Y is H, NH$_2$, NHCH$_3$, N(CH$_3$)$_2$, C$_1$-C$_4$ alkyl, C$_1$-C$_4$ alkyl substituted with 1-3 atoms of (a) F, (b) Cl or (c) Br, CH$_2$OCH$_3$, CH$_2$OC$_2$H$_5$, C$_1$-C$_4$ alkoxy, C$_1$-C$_2$ alkylthio, C$_3$-C$_4$ alkenyloxy, C$_3$-C$_4$ alkynyloxy, OCH$_2$CH$_2$OCH$_3$, OCH$_2$CH$_2$F, OCH$_2$CH$_2$Cl, OCH$_2$CH$_2$Br, OCH$_2$CF$_3$, CH(OCH$_3$)$_2$, CH(OC$_2$H$_5$)$_2$,

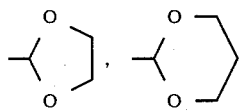

or OCF$_2$H;
Z is CH or N;
X$_1$ is O or CH$_2$;
Y$_1$ is H, CH$_3$, OCH$_3$ or Cl;
X$_2$ is CH$_3$, OCH$_3$ or SCH$_3$;
Y$_2$ is CH$_3$, C$_2$H$_5$ or CH$_2$CF$_3$; and
X$_3$ is CH$_3$ or OCH$_3$;
provided that
(1) when R$_3$ is CH$_3$, then R$_2$ is H or CH$_3$;
(2) when R$_4$ is CH$_3$, then R$_2$ is other than H; and
(3) when X is Cl or Br, then Z is CH and Y is NH$_2$, NHCH$_3$, N(CH$_3$)$_2$CH$_3$, OCH$_3$ or OCF$_2$H.

Preferred for their higher herbicidal activity, greater plant growth regulant activity and/or more favorable ease of synthesis are:

(1) Compounds of Formula I where A is A-1, A-2, A-3 or A-4, R is H and Y is NH$_2$, NHCH$_3$, N(CH$_3$)$_2$, CH$_3$, CH$_2$CH$_3$, CF$_3$, CH$_2$F, CH$_2$OCH$_3$CH$_2$OCH$_2$CH$_3$, OCH$_3$, OCH$_2$CH$_3$, SCH$_3$, OCH$_2$CH=CH$_2$, OCH$_2$C≡CH, OCH$_2$CF$_3$, CH(OCH$_3$)$_2$, CH(OCH$_2$CH$_3$)$_2$,

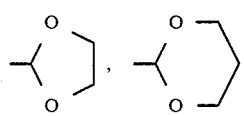

or OCF$_2$H;

(2) Compounds of Preferred 1 where R$_1$ is H or CH$_3$, R$_2$ is H or CH$_3$, R$_5$ is H, CH$_3$, OCH$_3$, SCH$_3$ or Cl and R$_6$ is H, CH$_3$, OCH$_3$, SCH$_3$ or Cl;

(3) Compounds of Preferred 2 where A is A-1, X is Cl, Br, CH$_3$ or OCH$_3$, Y is CH$_3$, OCH$_3$, CH$_2$OCH$_3$, OCH$_2$CH$_3$ or CH(OCH$_3$)$_2$, and R$_5$ and R$_6$ are H;

(4) Compounds of Preferred 3 where L is L-1;

(5) Compounds of Preferred 3 where L is L-2; and (6) Compounds of Preferred 3 where L is L-3.

Specifically preferred for their highest herbicidal activity, greatest plant growth regulant activity and/or more favorable ease of synthesis are the following:

2,3-Dihydro-N-[(4-methoxy-6-methyl-1,3,5-triazin-2-yl)aminocarbonyl]-1H-indole-7-sulfonamide, m.p. 165°-168° C.

2,3-Dihydro-N-[(4-methoxy-6-methyl-pyrimidin-2-yl)aminocarbonyl]-2-methyl-1H-indole-7-sulfonamide, m.p. 175°-177° C.

DETAILED DESCRIPTION OF THE INVENTION

Synthesis

The compounds of Formula I can be prepared as shown in Equation 1 by the reaction of the appropriately substituted sulfonamide of Formula II with the appropriate methyl carbamate of a heterocyclic compound of Formula III in the presence of an equimolar amount of trimethylaluminum.

Equation 1

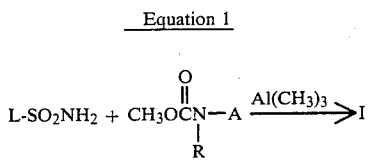

The reaction is carried out at 25° to 40° C. in a solvent such as methylene chloride for 10 to 96 hours under an inert atmosphere as taught in EPO Publication 82,681. The required carbamates III are prepared by reacting the corresponding amines with dimethylcarbonate or methyl chloroformate in the presence of a strong base.

Sulfonamides of Formula II where L is L-1 and R$_1$ is H can be prepared as shown in Equation 2.

Equation 2

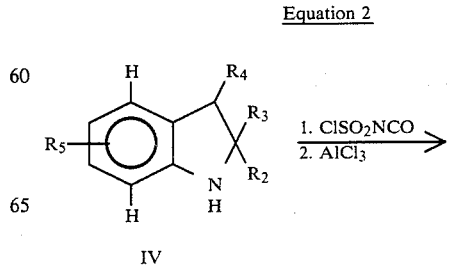

-continued
Equation 2

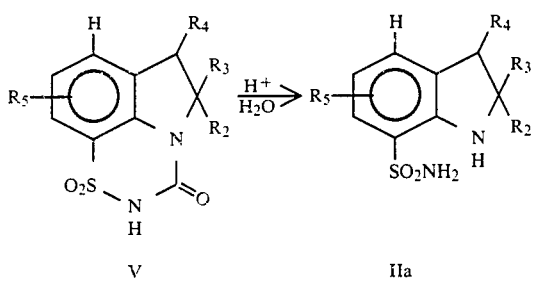

V    IIa

Following the general procedure of Y. Girard, J. G. Atkinson and J. Rokach, *J. Chem. Soc. Perkin I.* 1044 (1979), the appropriately substituted indoline in a solvent of nitromethane or nitroethane is treated with chlorosulfonyl isocyanate (CSI) at $-40°$ to $0°$ C. followed by warming to $25°$ C. Aluminum chloride is then added and the solution heated to $100°-120°$ for 1 to 4 hours. Addition of water results in the isolation of V. Hydrolysis of V in aqueous acid results in the isolation of IIa. Sulfonamides of Formula II where L is L-3 and $R_1$ is H can be prepared in a similar fashion from the corresponding tetrahydroquinolines.

Sulfonamides of Formula IIc where L is L-2 can be prepared by dehydrogenation of sulfonamides of Formula IIb where L is L-1 and $R_3$ is H, as shown in Equation 3.

Equation 3

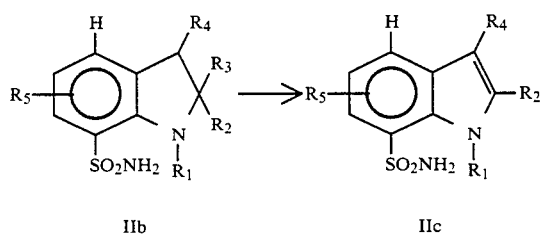

IIb    IIc

Both catalytic and chemical methods are effective in dehydrogenation of indolines to indoles. The most common reagents are palladium-on-charcoal, quinones such as chloranil and dichlorodicyanoquinone (DDQ) and manganese dioxide as described in *The Chemistry of Heterocyclic Compounds*, Vol. 25, "Indoles, Pt. 1", W. J. Houlihan Editor, Wiley-Interscience, 1972.

Sulfonamides of Formula IId where L is L-1 and $R_1$ is $C_1-C_3$ alkyl or $C_3$-alkenyl can be prepared as shown by example in Equation 4.

Equation 4

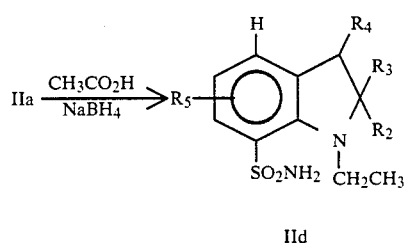

IId

The reaction of Equation 4 is carried out according to the procedures of G. W. Gribble et al., *J. Am. Chem. Soc.* (1974) 96, 7812. Sulfonamides of Formula II where L is L-3 and $R_1$ is $C_1-C_3$ alkyl or $C_3$-alkenyl can be prepared in a similar fashion.

Indolines of Formula IV where $R_3$ is H can be prepared from the corresponding indole by the procedure of G. W. Gribble and J. H. Hoffman, *Synthesis*, (1977) 859, as shown in Equation 5.

Equation 5

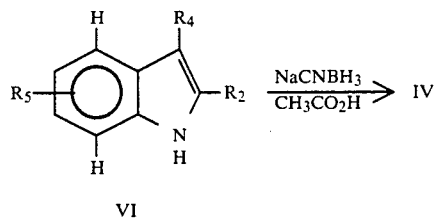

VI

Other methods of preparation of compounds of Formula IV are found in *The Chemistry of Heterocyclic Compounds* "Indoles" Pts. 1-4, Wiley-Interscience, as are the methods of preparation of the requisite compounds of Formula VI.

Tetrahydroquinolines of Formula VIII where $R_3$ is H can be prepared from the corresponding quinolines by the procedure of G. W. Gribble and P. W. Heald, *Synthesis* (1975) 650, as shown in Equation 6.

Equation 6

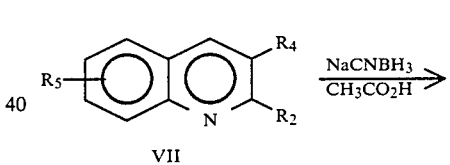

VII

VIII

Other methods of preparation of compounds of Formula VIII are found in *The Chemistry of Heterocyclic Compounds*, "Quinolines", Parts 1 and 2, G. Jones Editor, Wiley-Interscience, 1977, 1982, as are the methods of preparation of the requisite compounds of Formula VII.

Indolines of Formula IV where $R_2$ and $R_3$ are $CH_3$ can be prepared as described by Paol and Landenheimer, *Ber.* 25, 2974 (1892).

The carbamates of Formula III in Equation 1 are also important intermediates for the preparation of the compounds of this invention and are described below.

The pyrimidines and triazines of Formula (IIIa) to (IIId) below are either known or can be prepared by obvious methods by one skilled in the art.

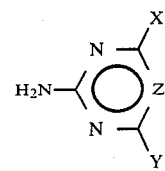 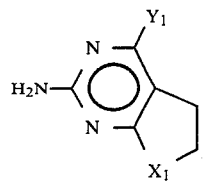

IIIa  IIIb

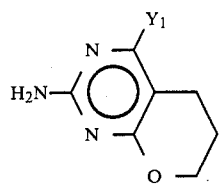 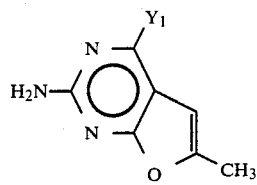

IIIc  IIId

For a review of the synthesis and reactions of 2-aminopyrimidines (IIIa, Z=CH) see *The Chemistry of Heterocyclic Compounds*, Vol. 16, John Wiley and Sons, New York (1962). For a review of the synthesis and reactions of 2-amino-s-triazines (IIIa, Z=N) see *The Chemistry of Heterocyclic Compounds*, Vol. 13, John Wiley, New York (1959), F. C. Schaefer, U.S. Pat. No. 3,154,547 and F. C. Schaefer and K. R. Huffman, *J. Org. Chem.*, 28, 1812 (1963). The synthesis of the bicyclic amines IIIb and IIIc is taught in European patent application No. 803,005,05.7. The synthesis of bicyclic amines IIId is taught in European patent publication 46,677.

The amines of Formula IIIa where X is $OCF_2H$ or $CF_3$ and Y is $OCF_2H$ can be prepared by methods taught in South African patent application No. 825,045, or by suitable modifications that would be obvious to one skilled in the art.

The pyrimidines of Formula IIIa (Z=CH) where Y is $-CH(OCH_3)_2$, $-CH(OCH_2CH_3)_2$,

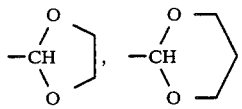

can be prepared according to the methods taught in European patent application No. 82306,492.8 or suitable modifications thereof known to one skilled in the art.

The triazine amines of Formula IIIe where $X_3$ is $CH_3$ or $OCH_3$ and R is H or $CH_3$ can be prepared according to the teachings of U.S. Ser. No. 472,879, filed Mar. 14, 1983.

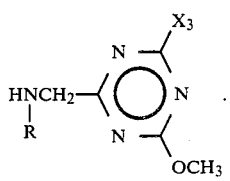

IIIe

Preparations of 3-amino-1,2,4-triazoles of Formula (IIIf) are known in the art and 1,2,4-triazoles are reviewed in *The Chemistry of Heterocyclic Compounds* "Triazoles 1,2,4" (John Wiley and Sons, New York, 1981).

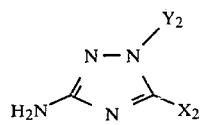

IIIf

Commonly used starting materials containing nitrogen are N-aminoguanidine, hydrazine, alkylhydrazines, cyanamide, ethyl cyanoacetimidate, dimethyl cyanodithioimidocarbonate, dimethyl cyanoimidocarbonate, ethoxymethylenecyanamide, and acylhydrazines. Some literature synthesis are illustrated below. Using these techniques or suitable modifications that would be apparent to one skilled in the art, the 3-amino-1,2,4-triazole intermediates can be readily prepared.

Heating equimolar amounts of ethyl propionimidate hydrochloride and N-aminoguanidine nitrate in pyridine gives 3-amino-5-ethyltriazole; German Pat. No. 1,073,499 (1960); *Berichte*, 96, 1064 (1963).

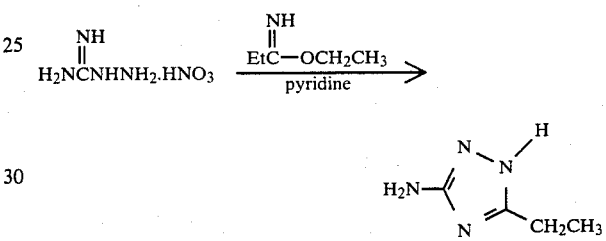

Condensation of hydrazine with ethyl N-cyanoacetimidate yields 3-amino-5-methyltriazole; *Journal of Organic Chemistry*, 28, 1816 (1963).

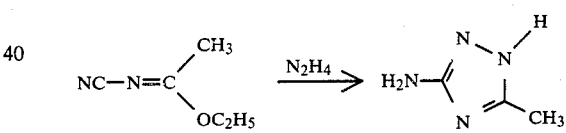

U.S. Pat. No. 2,835,581 (1958) teaches the preparation of 3-amino-5-(hydroxymethyl)triazole from N-aminoguanidine and glycolic acid and British Pat. No. 736,568 (1955) describes the synthesis of 3-amino-5-mercaptotriazole.

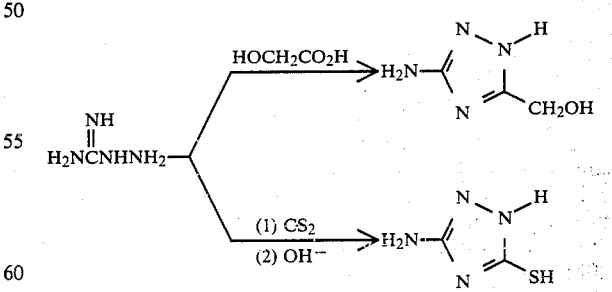

Condensing hydrazine with dimethyl cyanodithioimidocarbonate in acetonitrile gives 3-amino-5-methylthio-1,2,4-triazole while reaction of hydrazine with dimethyl N-cyanoimidocarbonate produces 3-amino-5-methoxy-1,2,4-triazole; *Journal of Organic Chemistry*, 39, 1522 (1974).

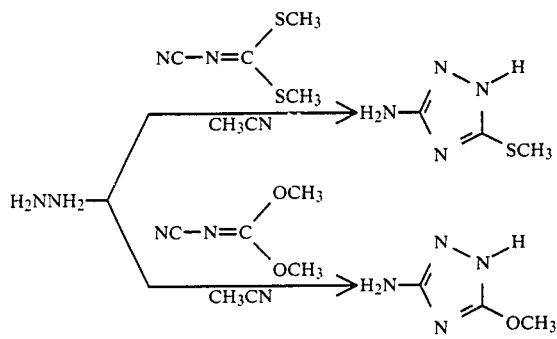

Reaction of substituted hydrazines with N-cyanothioimidocarbonates (prepared according to the procedure given in D. M. Wieland, Ph.D. Thesis, 1971, pp. 123-124) yields disubstituted aminotriazoles as shown below.

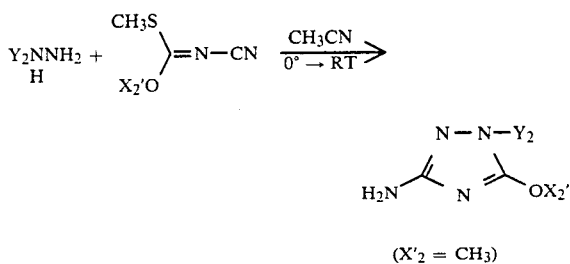

Many of the aminoheterocyclic intermediates where R is methyl may be prepared by a two-step procedure as described below.

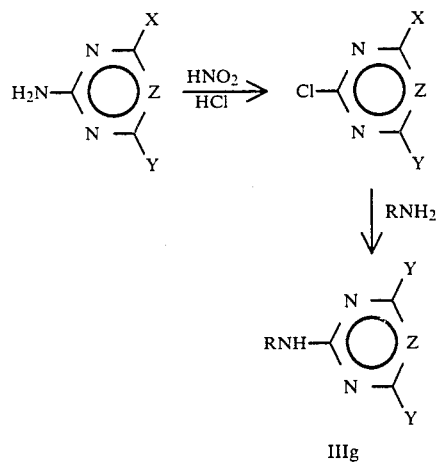

IIIg

A solution of the amine in concentrated hydrochloric acid is treated with sodium nitrite solution and the chloro compound is isolated in the usual manner by filtration of the acidic solution. A representative procedure is described by Bee and Rose in *J. Chem. Soc. C*, 2031 (1966), for the case in which Z=CH, and X=Y=OCH$_3$. Displacement of the chlorine may be accomplished by heating with an excess of methylamine in water to obtain the methylamino heterocycle (IIIg).

Agriculturally suitable salts of compounds of Formula I are also useful herbicides and can be prepared in a number of ways known to the art. For example, metal salts can be made by contacting compounds of Formula I with a solution of an alkali or alkaline earth metal salt having a sufficiently basic anion (e.g., hydroxide, alkoxide, carbonate or hydride). Quaternary amine salts can be made by similar techniques.

Salts of compounds of Formula I can also be prepared by exchange of one cation for another. Cationic exchange can be effected by direct contacting of an aqueous solution of a salt of a compound of Formula I (e.g., alkali metal or quaternary amine salt) with a solution containing the cation to be exchanged. This method is most effective when the desired salt containing the exchanged cation is insoluble in water, e.g., a copper salt, and can be separated by filtration.

Exchange may also be effected by passing an aqueous solution of a salt of a compound of Formula I (e.g., an alkali metal or quaternary amine salt) through a column packed with a cation exchange resin containing the cation to be exchanged. In this method, the cation of the resin is exchanged for that of the original salt and the desired product is eluted from the column. This method is particularly useful when the desired salt is water-soluble, e.g., a potassium, sodium or calcium salt.

Acid addition salts, useful in this invention, can be obtained by reacting a compound of Formula I with a suitable acid, e.g., p-toluenesulfonic acid, trichloroacetic acid or the like.

The compounds of this invention and their preparation are further illustrated by the following examples wherein temperatures are given in degrees centigrade and parts by weight unless otherwise indicated.

EXAMPLE 1

2,3-Dihydro-N-[(4-methoxy-6-methylpyrimidin-2-yl)aminocarbonyl]-2-methyl-1H-indole-7-sulfonamide To a solution of 2,3-dihydro-2-methyl-1H-indole-7-sulfonamide (1.0 g) and (4-methoxy-6-methylpyrimidin-2-yl)carbamic acid methyl ester (1.0 g) in methylene dichloride (100 ml) was added trimethylaluminum (3.0 ml of a 2.0 M solution in toluene). The mixture was heated at reflux for 18 hours under a nitrogen atmosphere. Work-up was achieved by careful addition of 100 ml of 1N HCl followed by separation of the organic layer. The methylene chloride was dried over MgSO$_4$ and evaporated to dryness. The residue was chromatographed on a silica gel column to give the pure product (0.2 g, m.p. 175°-177° C.).

IR (Nujol): 3400 and 1700 cm$^{-1}$. NMR: $\delta$ 1.2 (d, 3H), 2.4 (s, 3H), 3.2 (m, 3H), 4.0 (s, 3H), 6.3 (s, 1H), 6.6 (t, 1H), 7.2 (d, 1H), 7.5 (d, 1H).

EXAMPLE 2

2,3-Dihydro-2-methyl-1H-indole-7-sulfonamide

A slurry of 1,2-dihydro-2-methylpyrrolo[1,2,3-de][1,2,4]benzothiadiazin-4[5H]-one 6,6-dioxide (12.3 g) in a mixture of concentrated HCl (150 g) and water (125 g) was heated to reflux for 24 hours. The homogeneous solution was evaporated to dryness and the residue treated with water (100 ml) and sodium bicarbonate until no further foaming occurred. The crystalline product was isolated by filtration (9.12 g, m.p. 110°-112° C.).

IR (Nujol): 3200 cm$^{-1}$ and 3300 cm$^{-1}$ doublet. NMR: $\delta$ 1.4 (d, 3H), 2.75 (two doublets, 1H), 3.3 (two doublets, 1H), 4.3 (m, 1H), 4.95 (broad, 2H), 6.8 (m, 1H), 7.3 (d, 1H), 7.6 (d, 1H).

EXAMPLE 3

1,2-Dihydro-2-methylpyrrolo[1,2,3-de][1,2,4]benzothiadiazin-4[5H]-one, 6,6-dioxide To a solution of 2-methylindoline (8.0 g) in nitroethane (70 ml) at −60° C. was added slowly a solution of chlorosulfonyl isocyanate (6.15 ml) in nitroethane (10 ml). The mixture was slowly warmed to 0° C. when anhydrous aluminum chloride (10 g) was added in one portion. The mixture was heated to 110° C. for 30 minutes and then poured onto ice (300 g) and stirred until all the ice had melted. The crude product was filtered from the dark two phase mixture (6.34 g) and recrystallized from methanol (4.5 g, m.p. 215°–220° C.)

IR (Nujol): 1680 cm$^{-1}$. NMR: δ 1.5 (d, 3H), 2.9 (two doublets, 1H), 3.6 (two doublets, 1H), 4.7 (m, 1H), 7.1–7.7 (m, 3H).

EXAMPLE 4

2-Methylindoline

To a solution of 2-methylindole (61.2 g) in acetic acid (525 g) at 15° C. was added sodium cyanoborohydride (81 g) in portions. The reaction was then drowned in ice and water (1500 g) and the aqueous solution neutralized with sodium hydroxide (350 g). The mixture was extracted with 3 portions of ether (300 ml). The ether fractions were water washed, dried, and evaporated to give 57.4 g of an oil which was identical with an authentic sample by IR and TLC.

EXAMPLE 5

N-[(4-methoxy-6-methylpyrimidin-2-yl)aminocarbonyl]-1H-indole-7-sulfonamide

To a solution of 1H-indole-7-sulfonamide (1.0 g) and (4-methoxy-6-methylpyrimidin-2-yl)carbamic acid methyl ester (1.0 g) in methylene chloride (100 ml) was added trimethylaluminum (3.2 ml of a 2.0 M solution in toluene). The mixture was heated at reflux for 18 hours under a nitrogen atmosphere. Work-up was achieved by careful addition of 100 ml of 1N HCl followed by separation of the organic layer. The methylene chloride was dried over MgSO$_4$ and evaporated to an oil. The oil was dissolved in ether from which it quickly crystallized to give pure product (TLC) (0.56 g, m.p. 207°–209° C.).

IR (Nujol): 3400 and 1720 cm$^{-1}$. NMR: δ 2.4 (s, 3H), 3.9 (s, 3H), 6.4 (s, 1H), 6.6 (m, 1H), 7.2, (t, 1H), 7.5 (t, 1H), 7.8 (t (overlapping doublet), 2H).

EXAMPLE 6

1H-Indole-7-sulfonamide

To a slurry of activated manganese dioxide (20 g) in methylene chloride (200 ml) was added indoline-7-sulfonamide (4.3 g). The mixture was stirred at 25° C. for 24 hours. The solid was removed by filtration and the filtrate concentrated and hexane added until crystallization occurred. The pure product (TLC) was isolated by filtration (2.9 g, m.p. 125°–127° C.

IR (Nujol): 3250 cm$^{-1}$, 3400 cm$^{-1}$ doublet. NMR: δ 4.93 (s-broad, 2H), 6.65 (m-overlapping doublet, 1H), 7.2 (t, 2H), 7.34 (t, 1H), 7.69 (d, 1H), 7.85 (d, 1H), 9.4 (broad, 1H).

Using the procedures described above, the compounds described in Tables I–VIII may be prepared.

TABLE I

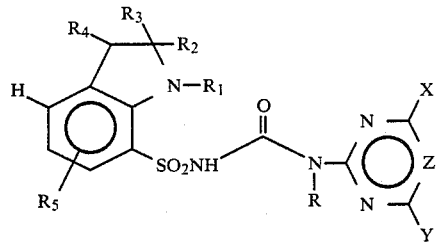

| R | R$_1$ | R$_2$ | R$_3$ | R$_4$ | R$_5$ | X | Y | Z | m.p. (°C.) |
|---|---|---|---|---|---|---|---|---|---|
| H | H | H | H | H | H | CH$_3$ | CH$_3$ | CH | 235–238 |
| H | H | H | H | H | H | CH$_3$ | OCH$_3$ | CH | 215–218 |
| H | H | H | H | H | H | OCH$_3$ | OCH$_3$ | CH | 155–158 |
| H | H | H | H | H | H | CH$_3$ | CH$_3$ | N | 220–222 |
| H | H | H | H | H | H | CH$_3$ | OCH$_3$ | N | 165–168 |
| H | H | H | H | H | H | OCH$_3$ | OCH$_3$ | N | 165–170 |
| CH$_3$ | H | H | H | H | H | OCH$_3$ | OCH$_3$ | CH | |
| H | CH$_3$ | H | H | H | H | CH$_3$ | CH$_3$ | CH | 177–178.5 |
| H | CH$_3$ | H | H | H | H | CH$_3$ | OCH$_3$ | CH | 209–210 |
| H | CH$_3$ | H | H | H | H | OCH$_3$ | OCH$_3$ | CH | 168.5–170.5 |
| H | CH$_3$ | H | H | H | H | CH$_3$ | CH$_3$ | N | 194–196 |
| H | CH$_3$ | H | H | H | H | CH$_3$ | OCH$_3$ | N | 165–166 |
| H | CH$_3$ | H | H | H | H | OCH$_3$ | OCH$_3$ | N | 185–186 |
| H | CH$_2$CH$_3$ | H | H | H | H | OCH$_3$ | OCH$_3$ | CH | |
| H | CH(CH$_3$)$_2$ | H | H | H | H | OCH$_3$ | OCH$_3$ | CH | |
| H | CH$_2$CH=CH$_2$ | H | H | H | H | OCH$_3$ | OCH$_3$ | CH | |
| H | H | CH$_3$ | H | H | H | CH$_3$ | CH$_3$ | CH | 149–150 |
| H | H | CH$_3$ | H | H | H | CH$_3$ | OCH$_3$ | CH | 175–177 |
| H | H | CH$_3$ | H | H | H | OCH$_3$ | OCH$_3$ | CH | 153–153.5 |
| H | H | CH$_3$ | H | H | H | CH$_3$ | CH$_3$ | N | 143–144 |
| H | H | CH$_3$ | H | H | H | CH$_3$ | OCH$_3$ | N | 147.5–148.5 |
| H | H | CH$_3$ | H | H | H | OCH$_3$ | OCH$_3$ | N | 144.5–145.5 |
| H | H | CH$_3$ | CH$_3$ | H | H | CH$_3$ | CH$_3$ | CH | |
| H | H | CH$_3$ | CH$_3$ | H | H | CH$_3$ | OCH$_3$ | CH | |
| H | H | CH$_3$ | CH$_3$ | H | H | OCH$_3$ | OCH$_3$ | CH | |

TABLE I-continued

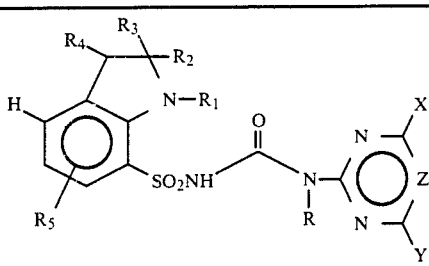

| R | R₁ | R₂ | R₃ | R₄ | R₅ | X | Y | Z | m.p. (°C.) |
|---|---|---|---|---|---|---|---|---|---|
| H | H | CH₃ | CH₃ | H | H | CH₃ | CH₃ | N | |
| H | H | CH₃ | CH₃ | H | H | CH₃ | OCH₃ | N | |
| H | H | CH₃ | CH₃ | H | H | OCH₃ | OCH₃ | N | |
| H | CH₃ | CH₃ | CH₃ | H | H | OCH₃ | OCH₃ | CH | |
| H | CH₃ | CH₃ | CH₃ | CH₃ | H | OCH₃ | OCH₃ | CH | |
| H | H | CH₃ | CH₃ | CH₃ | H | OCH₃ | OCH₃ | CH | |
| H | H | CH₂CH₃ | H | H | H | OCH₃ | OCH₃ | CH | |
| H | H | CH(CH₃)₂ | H | H | H | OCH₃ | OCH₃ | CH | |
| H | H | CO₂CH₃ | H | H | H | OCH₃ | OCH₃ | CH | |
| H | H | CO₂CH₂CH₃ | H | H | H | OCH₃ | OCH₃ | CH | |
| H | H | CON(CH₃)₂ | H | H | H | OCH₃ | OCH₃ | CH | |
| H | H | CH₃ | H | H | 5-CH₃ | OCH₃ | OCH₃ | N | |
| H | H | CH₃ | H | H | 5-C₂H₅ | OCH₃ | OCH₃ | CH | |
| H | H | CH₃ | H | H | 6-F | OCH₃ | OCH₃ | N | |
| H | H | CH₃ | H | H | 6-Cl | OCH₃ | OCH₃ | CH | |
| H | H | CH₃ | H | H | 5-Br | OCH₃ | OCH₃ | N | |
| H | H | CH₃ | H | H | 5-OCH₃ | OCH₃ | OCH₃ | CH | |
| H | H | CH₃ | H | H | 6-OCF₂H | OCH₃ | OCH₃ | N | |
| H | H | CH₃ | H | H | 5-SCH₃ | OCH₃ | OCH₃ | CH | |
| H | H | CH₃ | H | H | 6-SCF₂H | OCH₃ | OCH₃ | N | |
| H | H | CH₃ | H | H | 6-CF₃ | OCH₃ | OCH₃ | CH | |
| H | H | CH₃ | H | H | H | Cl | OCH₃ | CH | |
| H | H | CH₃ | H | H | H | Br | OCH₃ | CH | |
| H | H | CH₃ | H | H | H | C₂H₅ | OCH₃ | CH | |
| H | H | CH₃ | H | H | H | OC₂H₅ | OCH₃ | CH | |
| H | H | CH₃ | H | H | H | OCF₂H | OCH₃ | CH | |
| H | H | CH₃ | H | H | H | CF₃ | OCH₃ | CH | |
| H | H | CH₃ | H | H | H | OCH₃ | NH₂ | N | |
| H | H | CH₃ | H | H | H | OCH₃ | NHCH₃ | N | |
| H | H | CH₃ | H | H | H | OCH₃ | N(CH₃)₂ | N | |
| H | H | CH₃ | H | H | H | OCH₃ | C₂H₅ | CH | |
| H | H | CH₃ | H | H | H | OCH₃ | n-C₄H₉ | CH | |
| H | H | CH₃ | H | H | H | OCH₃ | CH₂CF₃ | CH | |
| H | H | CH₃ | H | H | H | OCH₃ | CH₂CH₂Cl | CH | |
| H | H | CH₃ | H | H | H | OCH₃ | CH₂CH₂Br | CH | |
| H | H | CH₃ | H | H | H | CH₃ | CH₂OCH₃ | CH | |
| H | H | CH₃ | H | H | H | CH₃ | CH₂OC₂H₅ | CH | |
| H | H | CH₃ | H | H | H | CH₃ | O—n-C₄H₉ | CH | |
| H | H | CH₃ | H | H | H | CH₃ | SCH₃ | CH | |
| H | H | CH₃ | H | H | H | CH₃ | OCH₂CH=CHCH₃ | CH | |
| H | H | CH₃ | H | H | H | CH₃ | OCH₂C≡CH | CH | |
| H | H | CH₃ | H | H | H | CH₃ | OCH₂CH₂OCH₃ | CH | |
| H | H | CH₃ | H | H | H | CH₃ | OCH₂CH₂F | CH | |
| H | H | CH₃ | H | H | H | CH₃ | OCH₂CH₂Cl | CH | |
| H | H | CH₃ | H | H | H | CH₃ | OCH₂CH₂Br | CH | |
| H | H | CH₃ | H | H | H | CH₃ | OCH₂CF₃ | CH | |
| H | H | CH₃ | H | H | H | CH₃ | CH(OCH₃)₂ | CH | |
| H | H | CH₃ | H | H | H | CH₃ | CH(OC₂H₅)₂ | CH | |
| H | H | CH₃ | H | H | H | CH₃ | (1,3-dioxolan-2-yl) | CH | |
| H | H | CH₃ | H | H | H | CH₃ | (1,3-dioxan-2-yl) | CH | |
| H | H | CH₃ | H | CH₃ | H | CH₃ | CH₃ | CH | 149.5–150.5 |
| H | H | CH₃ | H | CH₃ | H | CH₃ | OCH₃ | CH | 145.5–147.5 |
| H | H | CH₃ | H | CH₃ | H | OCH₃ | OCH₃ | CH | 159–160 |
| H | H | CH₃ | H | CH₃ | H | CH₃ | CH₃ | N | 102–107.5 |
| H | H | CH₃ | H | CH₃ | H | CH₃ | OCH₃ | N | 115–118 |

TABLE ii

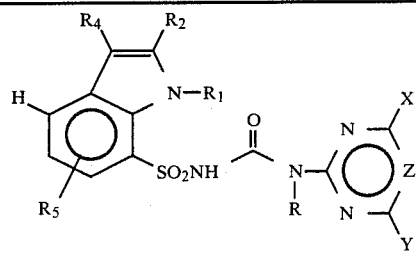

| R | R₁ | R₂ | R₄ | R₅ | X | Y | Z | m.p. (°C.) |
|---|---|---|---|---|---|---|---|---|
| H | H | H | H | H | CH₃ | CH₃ | CH | |
| H | H | H | H | H | CH₃ | OCH₃ | CH | 207–209.5 |
| H | H | H | H | H | OCH₃ | OCH₃ | CH | 189–190 |
| H | H | H | H | H | CH₃ | CH₃ | N | |
| H | H | H | H | H | CH₃ | OCH₃ | N | 156–157 |
| H | H | H | H | H | OCH₃ | OCH₃ | N | |
| CH₃ | H | H | H | H | OCH₃ | OCH₃ | CH | |
| H | CH₃ | H | H | H | CH₃ | CH₃ | CH | |
| H | CH₃ | H | H | H | CH₃ | OCH₃ | CH | |
| H | CH₃ | H | H | H | OCH₃ | OCH₃ | CH | |
| H | CH₃ | H | H | H | CH₃ | CH₃ | N | |
| H | CH₃ | H | H | H | CH₃ | OCH₃ | N | |
| H | CH₃ | H | H | H | OCH₃ | OCH₃ | N | |
| H | CH₂CH₃ | H | H | H | OCH₃ | OCH₃ | CH | |
| H | CH(CH₃)₂ | H | H | H | OCH₃ | OCH₃ | CH | |
| H | CH₂CH=CH₂ | H | H | H | OCH₃ | OCH₃ | CH | |
| H | H | CH₃ | H | H | CH₃ | CH₃ | CH | |
| H | H | CH₃ | H | H | CH₃ | OCH₃ | CH | |
| H | H | CH₃ | H | H | OCH₃ | OCH₃ | CH | |
| H | H | CH₃ | H | H | CH₃ | CH₃ | N | |
| H | H | CH₃ | H | H | CH₃ | OCH₃ | N | |
| H | H | CH₃ | H | H | OCH₃ | OCH₃ | N | |
| H | CH₃ | CH₃ | CH₃ | H | OCH₃ | OCH₃ | CH | |
| H | H | CH₃ | CH₃ | H | OCH₃ | OCH₃ | CH | |
| H | H | CH₂CH₃ | H | H | OCH₃ | OCH₃ | CH | |
| H | H | CH(CH₃)₂ | H | H | OCH₃ | OCH₃ | CH | |
| H | H | CO₂CH₃ | H | H | OCH₃ | OCH₃ | CH | |
| H | H | CO₂CH₂CH₃ | H | H | OCH₃ | OCH₃ | CH | |
| H | H | CON(CH₃)₂ | H | H | OCH₃ | OCH₃ | CH | |
| H | H | CH₃ | H | 5-CH₃ | OCH₃ | OCH₃ | N | |
| H | H | CH₃ | H | 5-C₂H₅ | OCH₃ | OCH₃ | CH | |
| H | H | CH₃ | H | 6-F | OCH₃ | OCH₃ | N | |
| H | H | CH₃ | H | 6-Cl | OCH₃ | OCH₃ | CH | |
| H | H | CH₃ | H | 5-Br | OCH₃ | OCH₃ | N | |
| H | H | CH₃ | H | 5-OCH₃ | OCH₃ | OCH₃ | CH | |
| H | H | CH₃ | H | 6-OCF₂H | OCH₃ | OCH₃ | N | |
| H | H | CH₃ | H | 5-SCH₃ | OCH₃ | OCH₃ | CH | |
| H | H | CH₃ | H | 6-SCF₂H | OCH₃ | OCH₃ | N | |
| H | H | CH₃ | H | 6-CF₃ | OCH₃ | OCH₃ | CH | |
| H | H | CH₃ | H | H | Cl | OCH₃ | CH | |
| H | H | CH₃ | H | H | Br | OCH₃ | CH | |
| H | H | CH₃ | H | H | C₂H₅ | OCH₃ | CH | |
| H | H | CH₃ | H | H | OC₂H₅ | OCH₃ | CH | |
| H | H | CH₃ | H | H | OCF₂H | OCH₃ | CH | |
| H | H | CH₃ | H | H | CF₃ | OCH₃ | CH | |
| H | H | CH₃ | H | H | OCH₃ | NH₂ | N | |
| H | H | CH₃ | H | H | OCH₃ | NHCH₃ | N | |
| H | H | CH₃ | H | H | OCH₃ | N(CH₃)₂ | N | |
| H | H | CH₃ | H | H | OCH₃ | C₂H₅ | CH | |
| H | H | CH₃ | H | H | OCH₃ | n-C₄H₉ | CH | |
| H | H | CH₃ | H | H | OCH₃ | CH₂CF₃ | CH | |
| H | H | CH₃ | H | H | OCH₃ | CH₂CH₂Cl | CH | |
| H | H | CH₃ | H | H | OCH₃ | CH₂CH₂Br | CH | |
| H | H | CH₃ | H | H | CH₃ | CH₂OCH₃ | CH | |
| H | H | CH₃ | H | H | CH₃ | CH₂OC₂H₅ | CH | |
| H | H | CH₃ | H | H | CH₃ | O—n-C₄H₉ | CH | |
| H | H | CH₃ | H | H | CH₃ | SCH₃ | CH | |
| H | H | CH₃ | H | H | CH₃ | OCH₂CH=CH₂ | CH | |
| H | H | CH₃ | H | H | CH₃ | OCH₂C≡CH | CH | |
| H | H | CH₃ | H | H | CH₃ | OCH₂CH₂OCH₃ | CH | |
| H | H | CH₃ | H | H | CH₃ | OCH₂CH₂F | CH | |
| H | H | CH₃ | H | H | CH₃ | OCH₂CH₂Cl | CH | |
| H | H | CH₃ | H | H | CH₃ | OCH₂CH₂Br | CH | |
| H | H | CH₃ | H | H | CH₃ | OCH₂CF₃ | CH | |
| H | H | CH₃ | H | H | CH₃ | CH(OCH₃)₂ | CH | |
| H | H | CH₃ | H | H | CH₃ | CH(OC₂H₅)₂ | CH | |

TABLE ii-continued

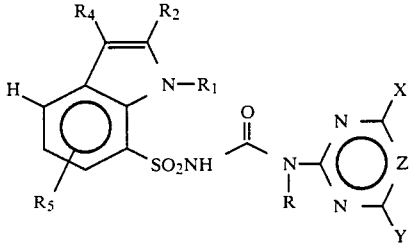

| R | R₁ | R₂ | R₄ | R₅ | X | Y | Z | m.p. (°C.) |
|---|----|----|----|----|----|----|----|------------|
| H | H | CH₃ | H | H | CH₃ | (1,3-dioxolan-2-yl) | CH | |
| H | H | CH₃ | H | H | CH₃ | (1,3-dioxan-2-yl) | CH | |

TABLE III

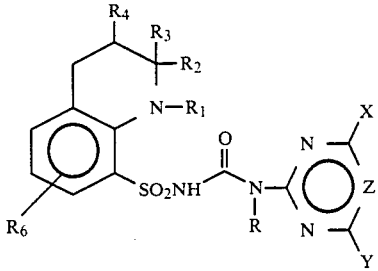

| R | R₁ | R₂ | R₃ | R₄ | R₆ | X | Y | Z | m.p. (°C.) |
|---|----|----|----|----|----|----|----|----|------------|
| H | H | H | H | H | H | CH₃ | CH₃ | CH | 213–215 |
| H | H | H | H | H | H | CH₃ | OCH₃ | CH | 200–202 |
| H | H | H | H | H | H | OCH₃ | OCH₃ | CH | 150–151 |
| H | H | H | H | H | H | CH₃ | CH₃ | N | 162–164 |
| H | H | H | H | H | H | CH₃ | OCH₃ | N | |
| H | H | H | H | H | H | OCH₃ | OCH₃ | N | 150–152 |
| CH₃ | H | H | H | H | H | OCH₃ | OCH₃ | CH | |
| H | CH₃ | H | H | H | H | CH₃ | CH₃ | CH | |
| H | CH₃ | H | H | H | H | CH₃ | OCH₃ | CH | |
| H | CH₃ | H | H | H | H | OCH₃ | OCH₃ | N | |
| H | CH₃ | H | H | H | H | CH₃ | CH₃ | N | |
| H | CH₃ | H | H | H | H | CH₃ | OCH₃ | N | |
| H | CH₃ | H | H | H | H | OCH₃ | OCH₃ | N | |
| H | CH₂CH₃ | H | H | H | H | OCH₃ | OCH₃ | CH | |
| H | CH(CH₃)₂ | H | H | H | H | OCH₃ | OCH₃ | CH | |
| H | CH₂CH=CH₂ | H | H | H | H | OCH₃ | OCH₃ | CH | |
| H | H | CH₃ | H | H | H | CH₃ | CH₃ | CH | 156–156.5 |
| H | H | CH₃ | H | H | H | CH₃ | OCH₃ | CH | 172.5–173 |
| H | H | CH₃ | H | H | H | OCH₃ | OCH₃ | CH | 153–154 |
| H | H | CH₃ | H | H | H | CH₃ | CH₃ | N | 136.5–137.5 |
| H | H | CH₃ | H | H | H | CH₃ | OCH₃ | N | 136.5–137 |
| H | H | CH₃ | H | H | H | OCH₃ | OCH₃ | N | 137–139 |
| H | H | CH₃ | CH₃ | H | H | CH₃ | CH₃ | CH | |
| H | H | CH₃ | CH₃ | H | H | CH₃ | OCH₃ | CH | |
| H | H | CH₃ | CH₃ | H | H | OCH₃ | OCH₃ | CH | |
| H | H | CH₃ | CH₃ | H | H | CH₃ | CH₃ | N | |
| H | H | CH₃ | CH₃ | H | H | CH₃ | OCH₃ | N | |
| H | H | CH₃ | CH₃ | H | H | OCH₃ | OCH₃ | N | |
| H | CH₃ | CH₃ | CH₃ | H | H | OCH₃ | OCH₃ | CH | |
| H | CH₃ | CH₃ | CH₃ | CH₃ | H | OCH₃ | OCH₃ | CH | |
| H | H | CH₃ | CH₃ | CH₃ | H | OCH₃ | OCH₃ | CH | |
| H | H | C₂H₅ | H | H | H | OCH₃ | OCH₃ | CH | |
| H | H | CH₂CH₃ | H | H | H | OCH₃ | OCH₃ | CH | |
| H | H | CH(CH₃)₂ | H | H | H | OCH₃ | OCH₃ | CH | |
| H | H | CO₂CH₃ | H | H | H | OCH₃ | OCH₃ | CH | |
| H | H | CO₂C₂H₅ | H | H | H | OCH₃ | OCH₃ | CH | |
| H | H | CON(CH₃)₂ | H | H | H | OCH₃ | OCH₃ | CH | |

TABLE III-continued

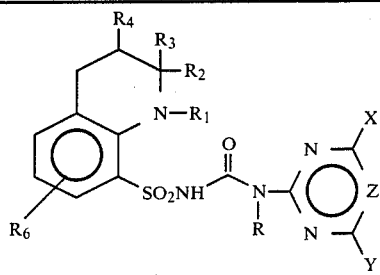

| R | R₁ | R₂ | R₃ | R₄ | R₆ | X | Y | Z | m.p. (°C.) |
|---|---|---|---|---|---|---|---|---|---|
| H | H | CH₃ | H | H | 6-CH₃ | OCH₃ | OCH₃ | N | |
| H | H | CH₃ | H | H | 6-C₂H₅ | OCH₃ | OCH₃ | CH | |
| H | H | CH₃ | H | H | 7-F | OCH₃ | OCH₃ | N | |
| H | H | CH₃ | H | H | 7-Cl | OCH₃ | OCH₃ | CH | |
| H | H | CH₃ | H | H | 6-Br | OCH₃ | OCH₃ | N | |
| H | H | CH₃ | H | H | 6-OCH₃ | OCH₃ | OCH₃ | CH | |
| H | H | CH₃ | H | H | 7-OCF₂H | OCH₃ | OCH₃ | N | |
| H | H | CH₃ | H | H | 6-SCH₃ | OCH₃ | OCH₃ | CH | |
| H | H | CH₃ | H | H | 7-SCF₂H | OCH₃ | OCH₃ | N | |
| H | H | CH₃ | H | H | 7-CF₃ | OCH₃ | OCH₃ | CH | |
| H | H | CH₃ | H | H | H | Cl | OCH₃ | CH | |
| H | H | CH₃ | H | H | H | Br | OCH₃ | CH | |
| H | H | CH₃ | H | H | H | C₂H₅ | OCH₃ | CH | |
| H | H | CH₃ | H | H | H | OC₂H₅ | OCH₃ | CH | |
| H | H | CH₃ | H | H | H | OCF₂H | OCH₃ | CH | |
| H | H | CH₃ | H | H | H | CF₃ | OCH₃ | CH | |
| H | H | CH₃ | H | H | H | OCH₃ | NH₂ | N | |
| H | H | CH₃ | H | H | H | OCH₃ | NHCH₃ | N | |
| H | H | CH₃ | H | H | H | OCH₃ | N(CH₃)₂ | N | |
| H | H | CH₃ | H | H | H | OCH₃ | C₂H₅ | CH | |
| H | H | CH₃ | H | H | H | OCH₃ | n-C₄H₉ | CH | |
| H | H | CH₃ | H | H | H | OCH₃ | CH₂CF₃ | CH | |
| H | H | CH₃ | H | H | H | OCH₃ | CH₂CH₂Cl | CH | |
| H | H | CH₃ | H | H | H | OCH₃ | CH₂CH₂Br | CH | |
| H | H | CH₃ | H | H | H | CH₃ | CH₂OCH₃ | CH | |
| H | H | CH₃ | H | H | H | CH₃ | CH₂OC₂H₅ | CH | |
| H | H | CH₃ | H | H | H | CH₃ | O—n-C₄H₉ | CH | |
| H | H | CH₃ | H | H | H | CH₃ | SCH₃ | CH | |
| H | H | CH₃ | H | H | H | CH₃ | OCH₂CH=CH₂CH₃ | CH | |
| H | H | CH₃ | H | H | H | CH₃ | OCH₂C≡CH | CH | |
| H | H | CH₃ | H | H | H | CH₃ | OCH₂CH₂OCH₃ | CH | |
| H | H | CH₃ | H | H | H | CH₃ | OCH₂CH₂F | CH | |
| H | H | CH₃ | H | H | H | CH₃ | OCH₂CH₂Cl | CH | |
| H | H | CH₃ | H | H | H | CH₃ | OCH₂CH₂Br | CH | |
| H | H | CH₃ | H | H | H | CH₃ | OCH₂CF₃ | CH | |
| H | H | CH₃ | H | H | H | CH₃ | CH(OCH₃)₂ | CH | |
| H | H | CH₃ | H | H | H | CH₃ | CH(OC₂H₅)₂ | CH | |
| H | H | CH₃ | H | H | H | CH₃ | (1,3-dioxolan-2-yl) | CH | |
| H | H | CH₃ | H | H | H | CH₃ | (1,3-dioxan-2-yl) | CH | |

TABLE IV

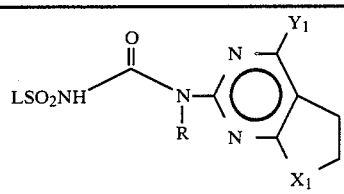 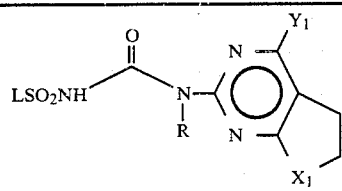

| L | R | R₁ | R₂ | R₃ | R₄ | R₅ | R₆ | X₁ | Y₁ | m.p. (°C.) | L | R | R₁ | R₂ | R₃ | R₄ | R₅ | R₆ | X₁ | Y₁ | m.p. (°C.) |
|---|---|---|---|---|---|---|---|---|---|---|---|---|---|---|---|---|---|---|---|---|---|
| L-1 | H | H | H | H | H | — | H | O | CH₃ | | L-1 | H | H | H | H | H | — | H | O | OCH₃ | |

TABLE IV-continued

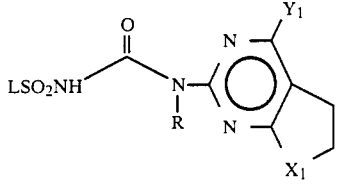

| L | R | R₁ | R₂ | R₃ | R₄ | R₅ | R₆ | X₁ | Y₁ | m.p. (°C.) |
|---|---|---|---|---|---|---|---|---|---|---|
| L-1 | H | H | H | H | H | H | — | CH₂ | CH₃ | |
| L-1 | H | H | H | H | H | H | — | CH₂ | OCH₃ | |
| L-1 | H | CH₃ | H | H | H | H | — | O | OCH₃ | |
| L-1 | H | CH₃ | H | H | H | H | — | CH₂ | OCH₃ | |
| L-1 | H | H | CH₃ | H | H | H | — | O | OCH₃ | |
| L-1 | H | H | CH₃ | H | H | H | — | CH₂ | OCH₃ | |
| L-1 | H | CH₃ | CH₃ | H | H | H | — | O | OCH₃ | |
| L-1 | H | CH₃ | CH₃ | H | H | H | — | CH₂ | OCH₃ | |
| L-1 | H | H | CH₃ | CH₃ | H | H | — | O | OCH₃ | |
| L-2 | H | H | H | — | H | H | — | O | CH₃ | |
| L-2 | H | H | H | — | H | H | — | O | OCH₃ | |
| L-2 | H | H | H | — | H | H | — | CH₂ | CH₃ | |
| L-2 | H | H | H | — | H | H | — | CH₂ | OCH₃ | |
| L-2 | H | CH₃ | H | — | H | H | — | O | OCH₃ | |
| L-2 | H | CH₃ | H | — | H | H | — | CH₂ | OCH₃ | |
| L-2 | H | H | CH₃ | — | H | H | — | O | OCH₃ | |
| L-2 | H | H | CH₃ | — | H | H | — | CH₂ | OCH₃ | |
| L-2 | H | CH₃ | CH₃ | — | H | H | — | O | OCH₃ | |
| L-2 | H | CH₃ | CH₃ | — | H | H | — | CH₂ | OCH₃ | |
| L-2 | H | CH₃ | — | — | CH₃ | H | — | O | OCH₃ | |
| L-3 | H | H | H | H | H | — | H | O | CH₃ | |
| L-3 | H | H | H | H | H | — | H | O | OCH₃ | |
| L-3 | H | H | H | H | H | — | H | CH₂ | CH₃ | |
| L-3 | H | H | H | H | H | — | H | CH₂ | OCH₃ | |
| L-3 | H | CH₃ | H | H | H | — | H | O | OCH₃ | |
| L-3 | H | CH₃ | H | H | H | — | H | CH₂ | OCH₃ | |
| L-3 | H | H | CH₃ | H | H | — | H | O | OCH₃ | |
| L-3 | H | H | CH₃ | H | H | — | H | CH₂ | OCH₃ | |
| L-3 | H | CH₃ | CH₃ | H | H | — | H | O | OCH₃ | |
| L-3 | H | CH₃ | CH₃ | H | H | — | H | CH₂ | OCH₃ | |
| L-3 | H | H | CH₃ | CH₃ | H | — | H | O | OCH₃ | |

TABLE V

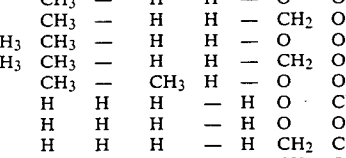

| L | R | R₁ | R₂ | R₃ | R₄ | R₅ | R₆ | Y₁ | m.p. (°C.) |
|---|---|---|---|---|---|---|---|---|---|
| L-1 | H | H | H | H | H | H | — | CH₃ | |
| L-1 | H | H | H | H | H | H | — | OCH₃ | |
| L-1 | H | H | H | H | H | H | — | Cl | |
| L-1 | H | CH₃ | H | H | H | H | — | CH₃ | |
| L-1 | H | CH₃ | H | H | H | H | — | OCH₃ | |
| L-1 | H | H | CH₃ | H | H | H | — | CH₃ | |
| L-1 | H | H | CH₃ | H | H | H | — | OCH₃ | |
| L-1 | H | CH₃ | CH₃ | H | H | H | — | CH₃ | |
| L-1 | H | CH₃ | CH₃ | H | H | H | — | OCH₃ | |
| L-1 | H | H | CH₃ | CH₃ | H | H | — | OCH₃ | |
| L-2 | H | H | H | — | H | H | — | CH₃ | |
| L-2 | H | H | H | — | H | H | — | OCH₃ | |
| L-2 | H | H | H | — | H | H | — | Cl | |
| L-2 | H | CH₃ | H | — | H | H | — | CH₃ | |
| L-2 | H | CH₃ | H | — | H | H | — | OCH₃ | |
| L-2 | H | H | CH₃ | — | H | H | — | CH₃ | |
| L-2 | H | H | CH₃ | — | H | H | — | OCH₃ | |
| L-2 | H | CH₃ | CH₃ | — | H | H | — | CH₃ | |
| L-2 | H | CH₃ | CH₃ | — | H | H | — | OCH₃ | |
| L-3 | H | H | H | H | H | — | H | CH₃ | |
| L-3 | H | H | H | H | H | — | H | OCH₃ | |
| L-3 | H | H | H | H | H | — | H | Cl | |
| L-3 | H | CH₃ | H | H | H | — | H | CH₃ | |
| L-3 | H | CH₃ | H | H | H | — | H | OCH₃ | |

TABLE V-continued

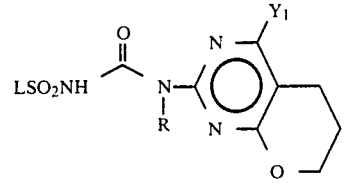

| L | R | R₁ | R₂ | R₃ | R₄ | R₅ | R₆ | Y₁ | m.p. (°C.) |
|---|---|---|---|---|---|---|---|---|---|
| L-3 | H | H | CH₃ | H | H | — | H | CH₃ | |
| L-3 | H | H | CH₃ | H | H | — | H | OCH₃ | |
| L-3 | H | CH₃ | CH₃ | H | H | — | H | CH₃ | |
| L-3 | H | CH₃ | CH₃ | H | H | — | H | OCH₃ | |
| L-3 | H | H | CH₃ | CH₃ | H | — | H | OCH₃ | |

TABLE VI

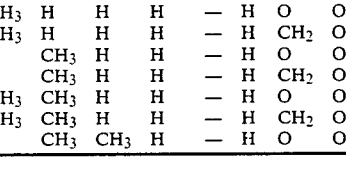

| L | R | R₁ | R₂ | R₃ | R₄ | R₅ | R₆ | Y₁ | m.p. (°C.) |
|---|---|---|---|---|---|---|---|---|---|
| L-1 | H | H | H | H | H | H | — | CH₃ | |
| L-1 | H | H | H | H | H | H | — | OCH₃ | |
| L-1 | H | H | H | H | H | H | — | Cl | |
| L-1 | H | CH₃ | H | H | H | H | — | CH₃ | |
| L-1 | H | CH₃ | H | H | H | H | — | OCH₃ | |
| L-1 | H | H | CH₃ | H | H | H | — | CH₃ | |
| L-1 | H | H | CH₃ | H | H | H | — | OCH₃ | |
| L-1 | H | CH₃ | CH₃ | H | H | H | — | CH₃ | |
| L-1 | H | CH₃ | CH₃ | H | H | H | — | OCH₃ | |
| L-1 | H | H | CH₃ | CH₃ | H | H | — | OCH₃ | |
| L-2 | H | H | H | — | H | H | — | CH₃ | |
| L-2 | H | H | H | — | H | H | — | OCH₃ | |
| L-2 | H | H | H | — | H | H | — | Cl | |
| L-2 | H | CH₃ | H | — | H | H | — | CH₃ | |
| L-2 | H | CH₃ | H | — | H | H | — | OCH₃ | |
| L-2 | H | H | CH₃ | — | H | H | — | CH₃ | |
| L-2 | H | H | CH₃ | — | H | H | — | OCH₃ | |
| L-2 | H | CH₃ | CH₃ | — | H | H | — | CH₃ | |
| L-2 | H | CH₃ | CH₃ | — | H | H | — | OCH₃ | |
| L-3 | H | H | H | H | H | — | H | CH₃ | |
| L-3 | H | H | H | H | H | — | H | OCH₃ | |
| L-3 | H | H | H | H | H | — | H | Cl | |
| L-3 | H | CH₃ | H | H | H | — | H | CH₃ | |
| L-3 | H | CH₃ | H | H | H | — | H | OCH₃ | |
| L-3 | H | H | CH₃ | H | H | — | H | CH₃ | |
| L-3 | H | H | CH₃ | H | H | — | H | OCH₃ | |
| L-3 | H | CH₃ | CH₃ | H | H | — | H | CH₃ | |
| L-3 | H | CH₃ | CH₃ | H | H | — | H | OCH₃ | |
| L-3 | H | H | CH₃ | CH₃ | H | — | H | OCH₃ | |

TABLE VII

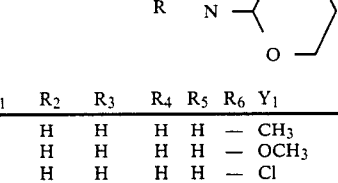

| L | R | R₁ | R₂ | R₃ | R₄ | R₅ | R₆ | X₂ | Y₂ | m.p. (°C.) |
|---|---|---|---|---|---|---|---|---|---|---|
| L-1 | H | H | H | H | H | H | — | CH₃ | C₂H₅ | |
| L-1 | H | H | H | H | H | H | — | OCH₃ | CH₃ | |
| L-1 | H | H | H | H | H | H | — | SCH₃ | CH₂CF₃ | |
| L-1 | H | CH₃ | H | H | H | H | — | CH₃ | C₂H₅ | |
| L-1 | H | CH₃ | H | H | H | H | — | OCH₃ | CH₃ | |
| L-1 | H | CH₃ | H | H | H | H | — | SCH₃ | CH₂CF₃ | |
| L-1 | H | H | CH₃ | H | H | H | — | CH₃ | C₂H₅ | |
| L-1 | H | H | CH₃ | H | H | H | — | OCH₃ | CH₃ | |
| L-1 | H | H | CH₃ | H | H | H | — | SCH₃ | CH₂CF₃ | |
| L-1 | H | CH₃ | CH₃ | H | H | H | — | CH₃ | C₂H₅ | |
| L-1 | H | CH₃ | CH₃ | H | H | H | — | OCH₃ | CH₃ | |

TABLE VII-continued

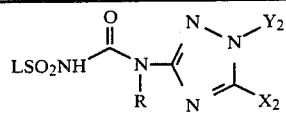

| L | R | R₁ | R₂ | R₃ | R₄ | R₅ | R₆ | X₂ | Y₂ | m.p. (°C.) |
|---|---|---|---|---|---|---|---|---|---|---|
| L-1 | H | CH₃ | CH₃ | H | H | H | — | SCH₃ | CH₂CF₃ | |
| L-1 | H | H | CH₃ | CH₃ | H | H | — | OCH₃ | CH₃ | |
| L-2 | H | H | H | — | H | H | — | CH₃ | C₂H₅ | |
| L-2 | H | H | H | — | H | H | — | OCH₃ | CH₃ | |
| L-2 | H | H | H | — | H | H | — | SCH₃ | CH₂CF₃ | |
| L-2 | H | CH₃ | H | — | H | H | — | CH₃ | CH₃ | |
| L-2 | H | CH₃ | H | — | H | H | — | OCH₃ | C₂H₅ | |
| L-2 | H | CH₃ | H | — | H | H | — | SCH₃ | CH₂CF₃ | |
| L-2 | H | H | CH₃ | — | H | H | — | CH₃ | CH₃ | |
| L-2 | H | H | CH₃ | — | H | H | — | OCH₃ | C₂H₅ | |
| L-2 | H | H | CH₃ | — | H | H | — | SCH₃ | CH₂CF₃ | |
| L-2 | H | CH₃ | CH₃ | — | H | H | — | CH₃ | CH₃ | |
| L-2 | H | CH₃ | CH₃ | — | H | H | — | OCH₃ | C₂H₅ | |
| L-2 | H | CH₃ | CH₃ | — | H | H | — | SCH₃ | CH₂CF₃ | |
| L-2 | H | CH₃ | — | CH₃ | H | — | OCH₃ | CH₃ | | |
| L-3 | H | H | H | H | H | H | H | CH₃ | C₂H₅ | |
| L-3 | H | H | H | H | H | — | H | OCH₃ | CH₃ | |
| L-3 | H | H | H | H | H | — | H | SCH₃ | CH₂CF₃ | |
| L-3 | H | CH₃ | H | H | H | — | H | CH₃ | C₂H₅ | |
| L-3 | H | CH₃ | H | H | H | — | H | OCH₃ | CH₃ | |
| L-3 | H | CH₃ | H | H | H | — | H | SCH₃ | CH₂CF₃ | |
| L-3 | H | H | CH₃ | H | H | — | H | CH₃ | C₂H₅ | |
| L-3 | H | H | CH₃ | H | H | — | H | OCH₃ | CH₃ | |
| L-3 | H | H | CH₃ | H | H | — | H | SCH₃ | CH₂CF₃ | |
| L-3 | H | CH₃ | CH₃ | H | H | — | H | CH₃ | C₂H₅ | |
| L-3 | H | CH₃ | CH₃ | H | H | — | H | OCH₃ | CH₃ | |
| L-3 | H | CH₃ | CH₃ | H | H | — | H | SCH₃ | CH₂CF₃ | |
| L-3 | H | H | CH₃ | CH₃ | H | — | H | OCH₃ | CH₃ | |

TABLE VIII

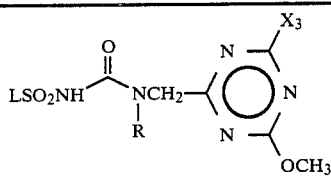

| L | R | R₁ | R₂ | R₃ | R₄ | R₅ | R₆ | X₃ | m.p. (°C.) |
|---|---|---|---|---|---|---|---|---|---|
| L-1 | H | H | H | H | H | H | — | CH₃ | |
| L-1 | H | H | H | H | H | H | — | OCH₃ | |
| L-1 | H | CH₃ | H | H | H | H | — | CH₃ | |
| L-1 | H | CH₃ | H | H | H | H | — | OCH₃ | |
| L-1 | H | H | CH₃ | H | H | H | — | CH₃ | |
| L-1 | H | H | CH₃ | H | H | H | — | OCH₃ | |
| L-1 | H | CH₃ | CH₃ | H | H | H | — | CH₃ | |
| L-1 | H | CH₃ | CH₃ | H | H | H | — | OCH₃ | |
| L-1 | H | H | CH₃ | CH₃ | H | H | — | CH₃ | |
| L-1 | H | H | CH₃ | CH₃ | H | H | — | OCH₃ | |
| L-1 | H | H | CH₃ | H | CH₃ | H | — | OCH₃ | |
| L-2 | H | H | H | — | H | H | — | CH₃ | |
| L-2 | H | H | H | — | H | H | — | OCH₃ | |
| L-2 | H | CH₃ | H | — | H | H | — | CH₃ | |
| L-2 | H | CH₃ | H | — | H | H | — | OCH₃ | |
| L-2 | H | H | CH₃ | — | H | H | — | CH₃ | |
| L-2 | H | H | CH₃ | — | H | H | — | OCH₃ | |
| L-2 | H | CH₃ | CH₃ | — | H | H | — | CH₃ | |
| L-2 | H | CH₃ | CH₃ | — | H | H | — | OCH₃ | |
| L-2 | H | H | CH₃ | — | CH₃ | H | — | CH₃ | |
| L-2 | H | H | CH₃ | — | CH₃ | H | — | OCH₃ | |
| L-2 | H | CH₃ | CH₃ | — | CH₃ | H | — | OCH₃ | |
| L-3 | H | H | H | H | H | — | H | CH₃ | |
| L-3 | H | H | H | H | H | — | H | OCH₃ | |
| L-3 | H | CH₃ | H | H | H | — | H | CH₃ | |
| L-3 | H | CH₃ | H | H | H | — | H | OCH₃ | |
| L-3 | H | H | CH₃ | H | H | — | H | CH₃ | |
| L-3 | H | H | CH₃ | H | H | — | H | OCH₃ | |
| L-3 | H | CH₃ | CH₃ | H | H | — | H | CH₃ | |
| L-3 | H | CH₃ | CH₃ | H | H | — | H | OCH₃ | |
| L-3 | H | H | CH₃ | CH₃ | H | — | H | CH₃ | |

TABLE VIII-continued

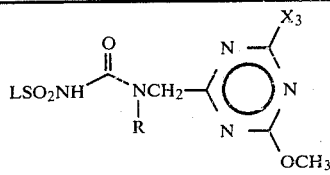

| L | R | R₁ | R₂ | R₃ | R₄ | R₅ | R₆ | X₃ | m.p. (°C.) |
|---|---|---|---|---|---|---|---|---|---|
| L-3 | H | H | CH₃ | CH₃ | H | — | H | OCH₃ | |
| L-3 | H | H | CH₃ | H | CH₃ | — | H | OCH₃ | |

Formulations

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly contain about 0.1% to 99% by weight of active ingredient(s) and at least one of (a) about 0.1% to 20% surfactant(s) and (b) about 1% to 99.9% solid or liquid diluent(s). More specifically they will contain these ingredients in the following approximate proportions:

TABLE IX

| | Weight Percent* | | |
|---|---|---|---|
| | Active Ingredient | Diluent(s) | Surfactant(s) |
| Wettable Powders | 20–90 | 0–74 | 1–10 |
| Oil Suspensions, Emulsions, Solutions, (including Emulsifiable Concentrates) | 3–50 | 40–95 | 0–15 |
| Aqueous Suspension | 10–50 | 40–84 | 1–20 |
| Dusts | 1–25 | 70–99 | 0–5 |
| Granules and Pellets | 0.1–95 | 5–99.9 | 0–15 |
| High Strength Compositions | 90–99 | 0–10 | 0–2 |

*Active ingredient plus at least one of a Surfactant or a Diluent equals 100 weight percent.

Lower or higher levels of active ingredient can course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books Caldwell, N.J., but other solids, either mined or manufactured, may be used. The more absorptive diluents are preferred for wettable powders and the denser ones for dusts. Typical liquid diluents and solvents are described in Marsden, "Solvents Guide", 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC publishing Corp., Ridgewood, N.J., as well as Sisely and Wood "Encyclopedia of Surface Active Agents", Chemical publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by sprayiny the active material upon preformed granular carriers or by agglomeration techniques. See J. E. Browning, "Agglomeration", *Chemical Engineering,* Dec. 4, 1967, pp. 147ff. and "Perry's Chemical Engineer's Handbook", 5th Ed., McGraw-Hill, New York, 1973, pp. 8-57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138-140, 162-164, 166, 167 and 169-182;

H. Gysin and E. Knusli, U.S. Pat. No. 2,891,855, June 23, 1959, Col. 3, line 66 through Col. 5, line 17 and Examples 1-4;

G. C. Klingman, "Weed Control as a Science", John Wiley and Sons, Inc., New York, 1961, pp. 81-96; and J. D. Fryer and S. A. Evans, "Weed Control Handbook", 5th Ed., Blackwell Scientific publications Oxford, 1968, pp. 101-103.

In the following examples, all parts are by weight unless otherwise indicated.

EXAMPLE 7

| Wettable Powder | |
|---|---|
| 2,3-Dihydro-N—[(4-methoxy-6-methylpyrimidin-2-yl)aminocarbonyl]-2-methyl-1H—indole-7-sulfonamide | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled until all the solids are essentially under 50 microns, reblended and packaged.

EXAMPLE 8

| Wettable Powder | |
|---|---|
| 2,3-Dihydro-N—[(4-methoxy-6-methylpyrimidin-2-yl)aminocarbonyl]-2-methyl-1H—indole-7-sulfonamide | 50% |
| sodium alkylnaphthalenesulfonate | 2% |
| low viscosity methyl cellulose | 2% |
| diatomaceous earth | 46% |

The ingredients are blended, coarsely hammer-milled and then air-milled to produce particles essentially all below 10 microns in diameter. The product is reblended before packaging.

EXAMPLE 9

| Granule | |
|---|---|
| Wettable Powder of Example 8 | 5% |
| attapulgite granules (U.S.S. 20-40 mesh; 0.84-0.42 mm) | 95% |

A slurry of wettable powder containing ≈25% solids is sprayed on the surface of attapulgite granules in a double-cone blender. The granules are dried and packaged.

EXAMPLE 10

| Extruded Pellet | |
|---|---|
| 2,3-Dihydro-N—[(4-methoxy-6-methyl-1,3,5-triazin-2-yl)-aminocarbonyl]-1H—indole-7-sulfonamide | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 11

| Oil Suspension | |
|---|---|
| 2,3-Dihydro-N—[(4-methoxy-6-methylpyrimidin-2-yl)-aminocarbonyl]-2-methyl-1H—indole-7-sulfonamide | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

EXAMPLE 12

| Wettable Powder | |
|---|---|
| 2,3-Dihydro-N—[(4-methoxy-6-methyl-1,3,5-triazin-2-yl)-aminocarbonyl]-1H—indole-7-sulfonamide | 20% |
| sodium alkylnaphthalenesulfonate | 4% |
| sodium ligninsulfonate | 4% |
| low viscosity methyl cellulose | 3% |
| attapulgite | 69% |

The ingredients are thoroughly blended. After grinding in a hammer-mill to produce particles essentially all below 100 microns the material is reblended and sifted through a U.S S. No. 50 sieve (0.3 mm opening) and packaged.

EXAMPLE 13

| Low Strength Granule | |
|---|---|
| 2,3-Dihydro-N—[(4-methoxy-6-methyl-1,3,5-triazin-2-yl)-aminocarbonyl]-1H—indole-7-sulfonamide | 1% |
| N,N—dimethylformamide | 9% |

| Low Strength Granule | |
|---|---|
| attapulgite granules (U.S.S. 20-40 sieve) | 90% |

The active ingredient is dissolved in the solvent and the solution is sprayed upon dedusted granules in a double cone blender. After spraying of the solution has been completed, the blender is allowed to run for a short period and then the granules are packaged.

EXAMPLE 14

| Aqueous Suspension | |
|---|---|
| 2,3-Dihydro-N—[(4-methoxy-6-methyl-1,3,5-triazin-2-yl)-aminocarbonyl]-1H—indole-7-sulfonamide | 40% |
| polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1.0% |
| water | 56.7% |

The ingredients are blended and ground together in a sand mill to produce particles essentially all under 5 microns in size.

EXAMPLE 15

| Solution | |
|---|---|
| 2,3-Dihydro-N—[(4-methoxy-6-methyl-1,3,5-triazin-2-yl)-aminocarbonyl]-1H-indole-7-sulfonamide | 5% |
| water | 95% |

The salt is added directly to the water with stirring to produce the solution, which may then be packaged for use.

EXAMPLE 16

| Low Strength Granule | |
|---|---|
| 2,3-Dihydro-N—[(4-methoxy-6-methylpyrimidin-2-yl)-aminocarbonyl]-2-methyl-1H—indole-7-sulfonamide | 0.1% |
| attapulgite granules (U.S.S. 20-40 mesh) | 99.9% |

The active ingredient is dissolved in a solvent and the solution is sprayed upon dedusted granules in a double-cone blender. After spraying of the solution has been completed, the material is warmed to evaporate the solvent. The material is allowed to cool and then packaged.

EXAMPLE 17

| Granule | |
|---|---|
| 2,3-Dihydro-N—[(4-methoxy-6-methylpyrimidin-2-yl)-aminocarbonyl]-2-methyl-1H—indole-7-sulfonamide | 80% |
| wetting agent | 1% |
| crude ligninsulfonate salt (containing 5-20% of the natural sugars) | 10% |
| attapulgite clay | 9% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued optionally with heat, until the water content is reduced to the desired level, generally less than 1%. The material is then discharged, screened to the desired size range, generally 14–100 mesh (1410–149 microns), and packaged for use.

EXAMPLE 18

| High Strength Concentrate | |
|---|---|
| 2,3-Dihydro-N—[(4-methoxy-6-methylpyrimidin-2-yl)-aminocarbonyl]-2-methyl-1H—indole-7-sulfonamide | 99% |
| silica aerogel | 0.5% |
| synthetic amorphous silica | 0.5% |

The ingredients are blended and ground in a hammer-mill to produce a material essentially all passing a U.S.S. No. 50 screen (0.3 mm opening). The concentrate may be formulated further if necessary.

EXAMPLE 19

| Wettable Powder | |
|---|---|
| 2,3-Dihydro-N—[(4-methoxy-6-methylpyrimidin-2-yl)-aminocarbonyl]-2-methyl-1H—indole-7-sulfonamide | 90% |
| dioctyl sodium sulfosuccinate | 0.1% |
| synthetic fine silica | 9.9% |

The ingredients are blended and ground in a hammer-mill to produce particles essentially all below microns. The material is sifted through a U.S.S. No. 50 screen and then packaged.

EXAMPLE 20

| Wettable Powder | |
|---|---|
| 2,3-Dihydro-N—[(4-methoxy-6-methyl-1,3,5-triazin-2-yl)-aminocarbonyl]-1H—indole-7-sulfonamide | 40% |
| sodium ligninsulfonate | 20% |
| montmorillonite clay | 40% |

The ingredients are thoroughly blended, coarsely hammer-milled and then air-milled to produce particles essentially all below 10 microns in size. The material is reblended and then packaged.

EXAMPLE 21

| Oil Suspension | |
|---|---|
| 2,3-Dihydro-N—[(4-methoxy-6-methylpyrimidin-2-yl)-aminocarbonyl]-1H-indole-7-sulfonamide | 35% |
| blend of polyalcohol carboxylic esters and oil soluble petroleum sulfonates | 6% |
| xylene | 59% |

The ingredients are combined and ground together in a sand mill to produce particles essentially all below 5 microns. The product can be used directly, extended with oils, or emulsified in water.

Utility

Test results indicate that the compounds of the present invention are active herbicides. They should have utility for broad-spectrum pre- and/or post-emergence weed control in areas where complete control of all vegetation is desired, such as around fuel storage tanks, ammunition depots, industrial storage areas, parking lots, drive-in theaters, around billboards, highway and railroad structures. Alternatively, many of the subject compounds should be useful for plant growth modification, such as growth retardation.

The rates of application for the compounds of the invention are determined by a number of factors, including their use as selective or general herbicides, the crop species involved, the types of weeds to be controlled, weather and climate, formulations selected, mode of application, amount of foliage present, etc. In general terms, the subject compounds should be applied at levels of around 0.05 to 10 kg/ha, the lower rates being suggested for use on lighter soils and/or those having a low organic matter content, for plant growth modification or for situations where only short-term persistence is required.

The compounds of the invention may be used in combination with any other commercial herbicide examples of which are those of the triazine, triazole, uracil, urea, amide, diphenylether, carbamate and bipyridylium types. The compounds may also be used in combination with mefluidide.

The herbicidal and plant growth modifying properties of the subject compounds were discovered in the greenhouse. The test procedures and results follow.

Compounds

Compound 1
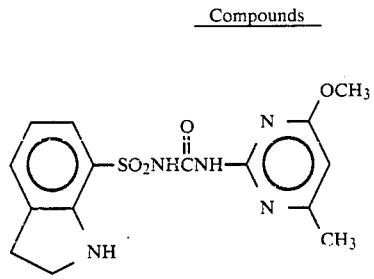

Compound 2
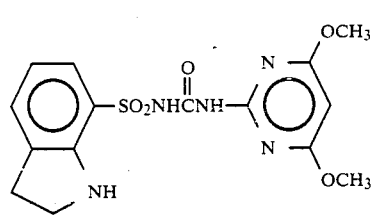

Compound 3
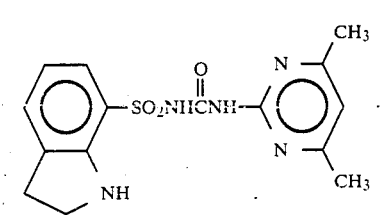

-continued

Compounds

Compound 4
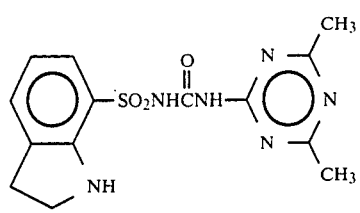

Compound 5
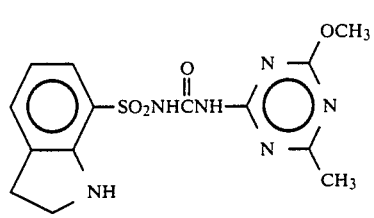

Compound 6
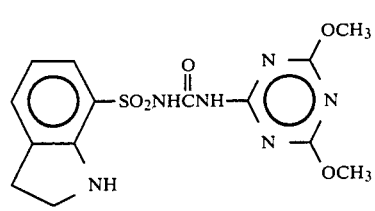

Compound 7
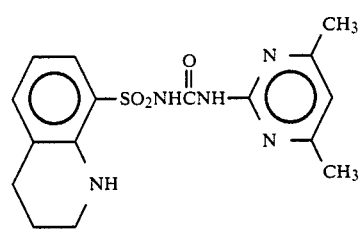

Compound 8
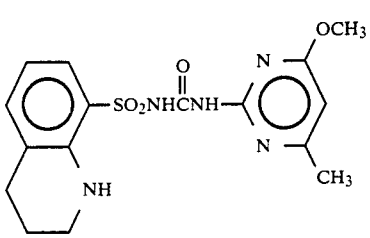

Compound 9
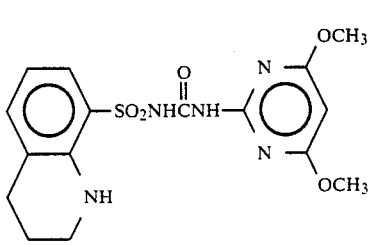

-continued
Compounds
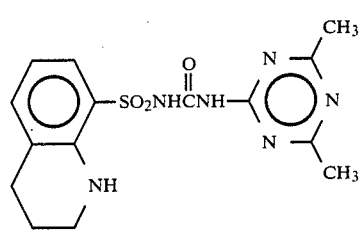
Compound 10
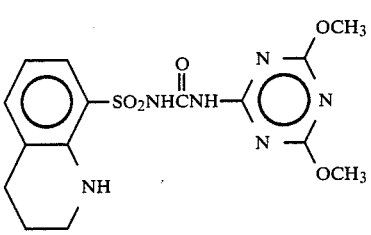
Compound 11
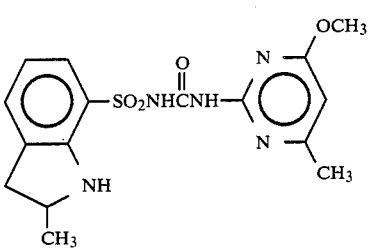
Compound 12
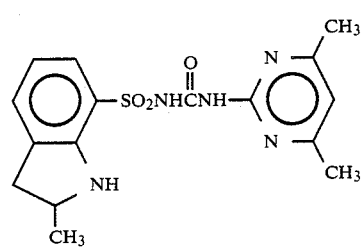
Compound 13
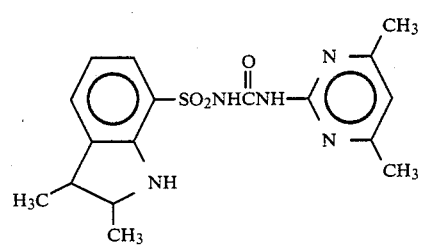
Compound 14
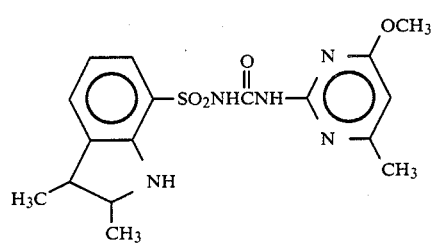
Compound 15
-continued
Compounds
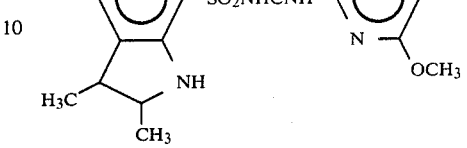
Compound 16
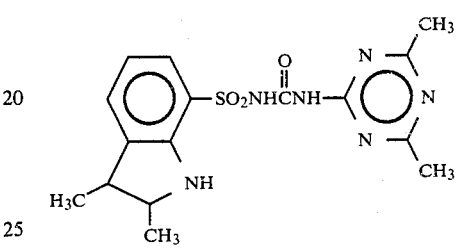
Compound 17
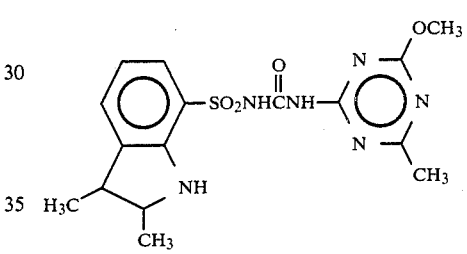
Compound 18
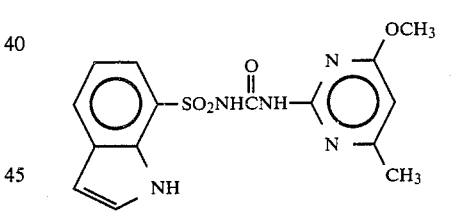
Compound 19
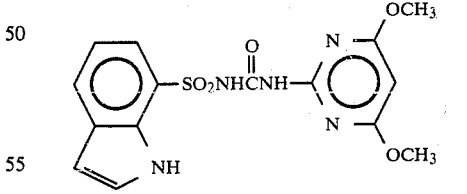
Compound 20
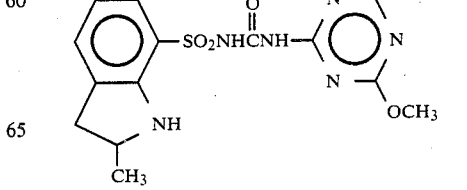
Compound 21

-continued
Compounds

Compound 22

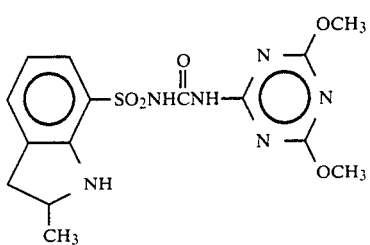

TEST A

Seeds of crabgrass (Digitaria sp.), barnyard-grass (Echinochloa crusgalli), wild oats (Avena fatua), sicklepod (Cassia obtusifolia), morningglory (Ipomoea sp.), cocklebur (Xanthium pensvlvanicum), sorghum, corn, soybean, cotton, sugar beet, rice, wheat and purple nutsedge (Cyperus rotundus) tubers were planted in a growth medium and treated pre-emergence with the chemicals dissolved in a non-phytotoxic solvent. At the same time, these crop and weed species were treated with a soil/foliage application. At the time of treatment, the plants ranged in height from 2 to 18 cm. Treated plants and controls were maintained in a greenhouse for sixteen days, after which all species were compared to controls and visually rated for response to treatment. The ratings, summarized in Table A, are based on a numerical scale extending from 0=no injury, to 10=complete kill. The accompanying descripti ve symbols have the following meanings:

C=chlorosis/necrosis;
E=emergence inhibition;
G=growth retardation;
H=formative effect;
X=axillary stimulation; and
U=unusual pigmentation.

Although some of the test compounds show low herbicidal activity at the low rate tested (50 g/ha), they would be expected to show increased herbicidal activity at higher application rates.

TABLE A

| Rate g/ha | Cmpd. 1 50 | Cmpd. 2 50 | Cmpd. 3 50 | Cmpd. 4 50 | Cmpd. 5 50 | Cmpd. 6 50 | Cmpd. 7 50 | Cmpd. 8 50 | Cmpd. 9 50 | Cmpd. 10 50 | Cmpd. 11 50 |
|---|---|---|---|---|---|---|---|---|---|---|---|
| POST-EMERGENCE | | | | | | | | | | | |
| Morningglory | 2C | 1C,3G | 0 | 0 | 1C,3G | 1C | 0 | 0 | 0 | 1C,3G | 1C |
| Cocklebur | 2G | 2G | 1H | 0 | 2C,5G | 2C,8G | 0 | 3C,8H | 3C,9H | 1C,4G | 9C |
| Sicklepod | 2C,2G | 1C,5G | 0 | 0 | 3C,5H | 2C,3H | 0 | 4C,7G | 3C,9G | 2C,4G | 4C,8G |
| Nutsedge | 5G | 7G | 5G | 0 | 3G | 0 | 0 | 5G,8X | 2C,9G | 2C,4G | 5G |
| Crabgrass | 0 | 0 | 0 | 0 | 2C,6G | 0 | 0 | 2C,4G | 0 | 0 | 5H |
| Barnyardgrass | 2H | 0 | 0 | 0 | 2C,9H | 2C,4H | 0 | 3C,6H | 3C,8H | 0 | 3C,8H |
| Wild Oats | 0 | 0 | 0 | 0 | 2G | 0 | 0 | 2G | 3G | 0 | 1C |
| Wheat | 0 | 0 | 0 | 0 | 0 | 0 | 0 | 2G | 3G | 0 | 1C |
| Corn | 1C,5H | 1H | 0 | 0 | 2C,7G | 3C,9G | 0 | 9H | 2C,9G, | 2U,9H | 9C |
| Soybean | 4C,9G | 2C,8G | 0 | 0 | 4C,9G | 3C,9G | 0 | 3C,9G | 3H,9G | 2H,8G,5X | 5C,9G |
| Rice | 2C,7G | 4G | 3G | 0 | 4C,9G | 4C,9G | 0 | 2C,9G | 3C,9G | 9G | 4C,9G |
| Sorghum | 2C,4G | 0 | 0 | 0 | 2C,9H | 3C,7G | 0 | 2C,7H | 2C,9G | 2C,8H | 4C,9H |
| Sugar beet | 5C,9G | 9C | 1H | 0 | 9C | 3C,7H | 0 | 3C,6H | 2C,8G | 3G | 5C,9G |
| Cotton | 4C,8G | 4C,8G | 2G | 0 | 4C,8G | 0 | 0 | 0 | 4G | 0 | 0 |
| PRE-EMERGENCE | | | | | | | | | | | |
| Morningglory | 7G | 8G | 0 | 0 | 7G | 0 | 0 | 0 | 4G | 0 | 8G |
| Cocklebur | 9H | 8H | 8G | 2H | 7G | 8G | 4H | 3C,9H | 3C,9H | 4G | 8H |
| Sicklepod | 8G | 7G | 0 | 0 | 9G | 8G | 0 | 3C,7H | 5G | 1C | 8G |
| Nutsedge | 5G | 8G | 0 | 0 | 0 | 0 | 0 | 0 | 0 | 0 | 0 |
| Crabgrass | 0 | 0 | 0 | 0 | 0 | 0 | 0 | 1C | 0 | 0 | 0 |
| Barnyardgrass | 1C | 1C | 0 | 0 | 2C | 0 | 0 | 3C,7H | 2C,2H | 1C | 3C,5G |
| Wild Oats | 2C,7G | 1C | 0 | 0 | 2C,5G | 0 | 0 | 3C,9G | 9G | 0 | 8G |
| Wheat | 2C,5G | 0 | 0 | 0 | 1C,3G | 0 | 0 | 7G | 5G | 0 | 2C,8G |
| Corn | 2C,8G | 2C,7G | 0 | 0 | 2C,8G | 2G | 0 | 3C,9G | 2C,9H | 2C,5G | 2C,8H |
| Soybean | 2C,3H | 1H | 0 | 0 | 4G | 1H | 0 | 3C,7H | 2C,4G | 0 | 3C,7H |
| Rice | 2C,7G | 2C,7G | 0 | 0 | 5C,9H | 4G | 0 | 3C,8H | 5C,9H | 2C,8G | 10E |
| Sorghum | 2C,8H | 2C,3G | 0 | 0 | 4C,9H | 6G | 0 | 3C,9H | 4C,9H | 2C,5G | 5C,9G |
| Sugar beet | 9G | 9G | 0 | 0 | 5C,9G | 3C,8G | 5G | 3C,9G | 3C,8G | 6G | 5C,9G |
| Cotton | 8G | 8G | 0 | 0 | 9G | 0 | 0 | 7G | 4G | 0 | 8G |

| Rate g/ha | Cmpd. 12 50 | Cmpd. 13 50 | Cmpd. 14 50 | Cmpd. 15 50 | Cmpd. 16 50 | Cmpd. 17 50 | Cmpd. 18 50 | Cmpd. 19 50 | Cmpd. 20 50 | Cmpd. 21 50 | Cmpd. 22 50 |
|---|---|---|---|---|---|---|---|---|---|---|---|
| POST-EMERGENCE | | | | | | | | | | | |
| Morningglory | 2C,7G | 2G | 0 | 1C | 0 | 0 | 0 | 1C | 0 | 5C,9G | 4H |
| Cocklebur | 5G | 7G | 0 | 2H | 0 | 0 | 0 | 2C,4G | 2C,6G | 6C,9G | 3C,9H |
| Sicklepod | 2C,8G | 1C | 0 | 0 | 0 | 0 | 0 | 0 | 2C,3G | 5C,9G | 3C,6G |
| Nutsedge | 8G | 5G | 0 | 0 | 0 | 0 | 0 | 2C | 8G | 3C,8G | 6G |
| Crabgrass | 3C,9G | 0 | 0 | 0 | 0 | 0 | 0 | 0 | 0 | 2C,5G | 6G |
| Barnyardgrass | 10C | 3C,8H | 0 | 0 | 0 | 0 | 0 | 3H | 0 | 2C,9H | 3C,8H |
| Wild Oats | 2C,8G | 2C,6G | 0 | 0 | 0 | 0 | 0 | 0 | 0 | 2C,5G | 2G |
| Wheat | 5G | 3G | 0 | 0 | 0 | 0 | 0 | 0 | 0 | 3G | 0 |
| Corn | 2C,9G | 2C,8H | 0 | 0 | 0 | 0 | 0 | 2H,4G | 0 | 9C | 2C,8H |
| Soybean | 3C,9G | 2C,7H | 0 | 1H | 0 | 0 | 2C,7G | 3C,8G | 4C,9G | 9C | 5C,9G |
| Rice | 3C,9G | 3C,8G | 0 | 0 | 0 | 0 | 0 | 2C,5G | 2G | 3C,9H | 4C,9G |
| Sorghum | 2C,9H | 3C,9H | 0 | 0 | 0 | 0 | 0 | 2C,5H | 0 | 9G | 2C,9H |
| Sugar beet | 9C | 3C,7H | 0 | 2C,3H | 0 | 0 | 2C,5G | 3C,7G | 3C,8G | 9C | 4C,9G |
| Cotton | 10C | 3C,9H | 0 | 0 | 0 | 0 | 0 | 0 | 2G | 9C | 4C,9G |
| PRE-EMERGENCE | | | | | | | | | | | |
| Morningglory | 8G | 2C,6H | 0 | 2C | 4G | 0 | 3G | 3H | 7G | 7G | 5G |

TABLE A-continued

| | | | | | | | | | | |
|---|---|---|---|---|---|---|---|---|---|---|
| Cocklebur | 9H | 5G | 3G | 2G | 5G | 0 | 3G | 8G | 8H | 8H | 8G |
| Sicklepod | 8G | 4G | 0 | 2G | 5G | 0 | 2G | 7G | 8G | 8G | 8G |
| Nutsedge | 5G | 0 | 0 | 0 | 0 | 0 | 0 | 5G | 0 | 5G | 0 |
| Crabgrass | 0 | 0 | 0 | 0 | 0 | 0 | 0 | 0 | 0 | 2G | 0 |
| Barnyardgrass | 3C,8G | 1C | 3C,3G | 2C,3H | 2C | 0 | 2C | 1C | 3C,2G | 2C,7G | 2C,3H |
| Wild Oats | 2C,7G | 0 | 0 | 2C | 0 | 0 | 0 | 2G | 0 | 2C,5G | 2G |
| Wheat | 6G | 0 | 0 | 2G | 0 | 0 | 0 | 0 | 0 | 0 | 0 |
| Corn | 2C,9G | 2C,6G | 0 | 2C,5G | 2C,4G | 0 | 2C,4G | 3G | 2C,6G | 4C,9H | 2C,7H |
| Soybean | 8H | 2C,3H | 0 | 2G | 0 | 0 | 0 | 1C | 2G | 9H | 7H |
| Rice | 3C,9H | 3C,7H | 3H | 5G | 4G | 0 | 3G | 3G | 5G | 10E | 9H |
| Sorghum | 3C,9H | 3C,9H | 0 | 5G | 2G | 0 | 0 | 4G | 0 | 6C,9H | 8H |
| Sugar beet | 3C,9H | 8G | 0 | 4G | 5G | 0 | 4G | 8G | 10E | 9G | 9G |
| Cotton | 5C,9G | 7G | 0 | 3G | 4G | 0 | 4G | 8G | 7G | 9G | 8G |

TEST B

Post-emergence

Two round pans (25 cm diameter by 12.5 cm deep) were filled with Woodstown sandy loam soil. One pan was planted with blackgrass (*Alopecurus myosuroides*) sugar beets, nutsedge (*Cyperus rotundus*) tubers, crabgrass (*Digitaria sanouinalis*), sicklepod (*Cassia obtusifolia*), teaweed (*Sida spinosa*), jimsonweed (*Datura stramonium*), velvetleaf (*Abutilon theophrasti*), and giant foxtail (*Setaria faberii*). The other pan was planted with wheat, cotton, rice, corn, soybean, wild oats (*Avena fatua*), cocklebur (*Xanthium pensylvanicum*), morningglory (*Ipomoea hederacea*), johnsongrass (*Sorghum halepenese*) and barnyardgrass (*Echinochloa crusgalli*). The plants were grown for approximately fourteen days, then sprayed post-emergence with the chemicals dissolved in a non-phytotoxic solvent.

Pre-emergence

Two round pans (25 cm diameter by 12.5 cm deep) were filled with Woodstown sandy loam soil. One pan was planted with blackgrass (*Alopecurus myosuroides*), sugar beets, nutsedge, crabgrass, sicklepod, teaweed, jimsonweed, velvetleaf, and giant foxtail. The other pan was planted with wheat, cotton, rice, corn, soybean, wild oats, cocklebur, morningglory, johnsongrass and barnyardgrass. The two pans were sprayed pre-emergence with the chemicals dissolved in a non-phytotoxic solvent.

Treated plants and controls were maintained in the greenhouse for 28 days, then all treated plants were compared to controls and visually rated for plant response.

Response ratings are based on a scale of 0 to 10: where 0=no effect, and 10=complete control. The type of response is indicated by letters where G=growth retardation.

Response ratings are contained in Table B.

TABLE B

| | Compound Number 2 | | | | | | Compound Number 5 | | | | | | Compound Number 12 | | | | | | |
|---|---|---|---|---|---|---|---|---|---|---|---|---|---|---|---|---|---|---|---|
| | Pre-Emergence | | Post-Emergence | | | | Pre-Emergence | | Post-Emergence | | | | Pre-Emergence | | | | Post-Emergence | | |
| Rate g/ha | 62 | 250 | 1 | 4 | 16 | 62 | 62 | 250 | 1 | 4 | 16 | 62 | 4 | 16 | 62 | 250 | 4 | 16 | 62 |
| Corn | 0 | 2G | 0 | 0 | 0 | 4G | 0 | 2G | 0 | 0 | 3G | 4G | 0 | 7G | 9G | 9G | 0 | 5G | 8G |
| Wheat | 0 | 0 | 0 | 0 | 0 | 0 | 0 | 0 | 0 | 0 | 0 | 0 | 0 | 0 | 4G | 0 | 0 | 0 | 0 |
| Rice | 2G | 6G | 0 | 0 | 2G | 5G | 4G | 7G | 0 | 0 | 0 | 4G | 0 | 3G | 9G | 10G | 0 | 4G | 8G |
| Soybean | 0 | 0 | 0 | 0 | 3G | 6G | 0 | 0 | 0 | 2G | 5G | 9G | 0 | 5G | 7G | 8G | 0 | 4G | 7G |
| Cotton | 0 | 0 | 0 | 0 | 2G | 5G | 0 | 3G | 0 | 2G | 4G | 6G | 0 | 3G | 5G | 9G | 0 | 4G | 9G |
| Sugar beet | 6G | 8G | 3G | 7G | 9G | 10G | 3G | 6G | 3G | 7G | 9G | 10G | 0 | 5G | 10G | 10G | 0 | 8G | 10C |
| Crabgrass | 0 | 3G | 0 | 0 | 0 | 3G | 0 | 0 | 0 | 0 | 0 | 3G | 0 | 0 | 5G | 7G | 0 | 0 | 0 |
| Johnsongrass | 0 | 0 | 0 | 0 | 0 | 0 | 0 | 0 | 0 | 0 | 0 | 4G | 0 | 0 | 6G | 9G | 0 | 3G | 7G |
| Blackgrass | 0 | 0 | 0 | 0 | 0 | 0 | 3G | 4G | 0 | 0 | 0 | 0 | 3G | 6G | 8G | 9G | 0 | 2G | 7G |
| Barnyardgrass | 0 | 0 | 0 | 0 | 0 | 0 | 0 | 0 | 0 | 0 | 0 | 0 | 0 | 2G | 7G | 9G | 0 | 3G | 7G |
| Nutsedge | 0 | 0 | 0 | 0 | 0 | 0 | 0 | 0 | 0 | 0 | 0 | 0 | 0 | 2G | 6G | 8G | 0 | 0 | 0 |
| Giant foxtail | 0 | 0 | 0 | 0 | 0 | 0 | 0 | 0 | 0 | 0 | 0 | 0 | — | — | — | — | 0 | 0 | 0 |
| Wild Oats | 0 | 0 | 0 | 0 | 0 | 0 | 0 | 0 | 0 | 0 | 0 | 0 | 0 | 0 | 3G | 8G | 0 | 0 | 0 |
| Cocklebur | 0 | 3G | 0 | 0 | 3G | 6G | 0 | 3G | 0 | 0 | 3G | 5G | 0 | 2G | 6G | 6G | 0 | 0 | 4G |
| Morningglory | 0 | 4G | 0 | 0 | 2G | 6G | 0 | 2G | 0 | 2G | 4G | 5G | 0 | 0 | 4G | 7G | 0 | 5G | 5G |
| Teaweed | 0 | 3G | 0 | 0 | 0 | 3G | 0 | 3G | 0 | 0 | 0 | 5G | 0 | 0 | 5G | 8G | 0 | 0 | 0 |
| Sicklepod | 0 | 3G | 0 | 0 | 3G | 5G | 0 | 3G | 0 | 0 | 0 | 6G | 0 | 2G | 7G | 8G | 0 | 0 | 0 |
| Jimsonweed | 0 | 4G | 0 | 0 | 2G | 7G | 0 | 2G | 0 | 0 | 2G | 5G | 2G | 7G | 8G | 9G | 0 | 0 | 8G |
| Velvetleaf | 0 | 2G | 0 | 0 | 0 | 6G | 0 | 3G | 0 | 0 | 0 | 4G | 2G | 5G | 8G | 9G | 0 | 4G | 8G |

What is claimed is:

1. A compound having the formula:

wherein

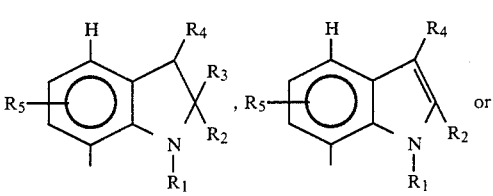

-continued

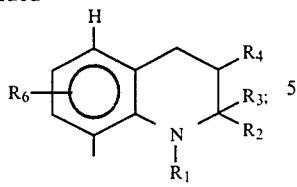
L-3

R is H or CH₃;
R₁ is H, C₁–C₃ alkyl or C₃ alkenyl;
R₂ is H, C₁–C₃ alkyl, CO₂R₇ or CON(CH₃)₂;
R₃ is H or CH₃;
R₄ is H of CH₃;
R₅ is H, CH₃, CH₂CH₃, F, Cl, Br, OCH₃, OCF₂H, SCH₃, SCF₂H or CF₃;
R₇ is CH₃ or CH₂CH₃;

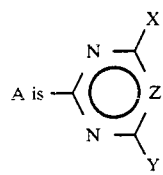 A-1

X is Cl, Br, C₁–C₂ alkyl, C₁–C₂ alkoxy, OCF₂H or CF₃;
Y is H, NH₂, NHCH₃, N(CH₃)₂, C₁–C₄ alkyl, C₁–C₄ alkyl substituted with 1–3 atoms of (a), F, (b) Cl or (c) Br, CH₂OCH₃, CH₂OC₂H₅, C₁-C₄ alkoxy, C₁–C₂ alkylthio, C₃–C₄ alkenyloxy, C₃–C₄ alkynyloxy, OCH₂CH₂OCH₃, OCH₂CH₂F, OCH₂CH₂Cl, OCH₂CH₂Br, OCH₂CF₃, CH(OCH₃)₂, CH(OC₂H₅)₂,

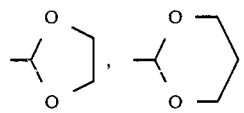

or OCF₂H;
Z is CH;
provided that
(1) when R₃ is CH₃, then R₂ is H or CH₃;
(2) when R₄ is CH₃, then R₂ is other than H; and
(3) when X is Cl or Br, then Y is NH₂, NHCH₃, N(CH₃)₂, CH₃, OCH₃ or OCF₂H.

2. A compound of claim 1 where R is H and Y is NH₂ NHCH₃, N(CH₃)₂, CH₃, CH₂CH₃, CF₃, CH₂F, CH₂OCH₃, CH₂OCH₂CH₃, OCH₃, OCH₂CH₃, SCH₃, OCH₂CH=CH₂, OCH₂C≡CH, OCH₂CF₃, CH(OCH₃)₂, CH(OCH₂CH₃)₂,

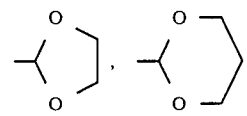

or OCF₂H.

3. A compound of claim 2 wherein R₁ is H or CH₃, R₂ is H or CH₃, R₅ is H, Ch₃, OCH₃, SCH₃ or Cl and R₆ is H, CH₃, OCH₃, SCH₃ or Cl.

4. A compound of claim 3 were X is Cl, Br, CH₃ or OCH₃, Y is CH₃, OCH₃, CH₂OCH₃, OCH₂CH₃ or CH(OCH₃)₂, and R₅ and R₆ are H.

5. A compound of claim 4 where L is L-1.

6. A compound of claim 4 where L is L-2.

7. A compound of claim 4 where L is L-3.

8. A compound of claim 1 which is 2,3-dihydro-N-[(4-methoxy-6-methyl-pyrimidin-2-yl)aminocarbonyl]-2-methyl-1H-indole-7-sulfonamide.

9. A composition suitable for controlling the growth of undesired vegetation which comprises a herbicidally effective amount of a compound of claim 1 and at least one of the following: surfactant, solid or liquid diluent.

10. A composition suitable for controlling the growth of undesired vegetation which comprises a herbicidally effective amount of a compound of claim 2 and at least one of the following: surfactant, solid or liquid diluent.

11. A composition suitable for controlling the growth of undesired vegatation which comprises a herbicidally effecitve amount of a compound of claim 3 and at least one of the following: surfactant, solid or liquid diluent.

12. A composition suitable for controlling the growth of undesired vegatation which comprises a herbicidally effective amount of a compound of claim 4 and at least one of the following: surfactant, solid or liquid diluent.

13. A method for the control of undesired vegatation which comprises applying to the locus of the undesired vegetation a herbicidally effective amount of a compound of claim 1.

14. A method for the control of undesired vegetation which comprises applying to the locus of the undesired vegetation a herbicidally effective amount of a compound of claim 2.

15. A method fo the control of undesired vegetation which comprises applying to the locus of the undesired vegetation a herbicidally effective amount of a compound of claim 3.

16. A method for the control of undesired vegetation which comprises applying to the locus of the undesired vegetation a herbicidally effective amount of a compound of claim 4.

* * * * *